United States Patent
Brocchini et al.

(10) Patent No.: US 7,220,414 B2
(45) Date of Patent: May 22, 2007

(54) DEGRADABLE POLYACETAL POLYMERS

(75) Inventors: Stephen J. Brocchini, Welwyn Garden (GB); Jorge Heller, Woodside, CA (US); Ryan Tomlinson, Cathays (GB); Ruth Duncan, Cardiff Bay (GB); Shane Garrett, Camden (GB); Marcus M. Klee, Selters/Ts (DE)

(73) Assignee: A.P. Pharma, Inc., Redwood City, CA (US)

( * ) Notice: Subject to any disclaimer, the term of this patent is extended or adjusted under 35 U.S.C. 154(b) by 912 days.

(21) Appl. No.: 09/949,162

(22) Filed: Sep. 6, 2001

(65) Prior Publication Data

US 2002/0082362 A1  Jun. 27, 2002

Related U.S. Application Data

(60) Provisional application No. 60/230,377, filed on Sep. 6, 2000.

(51) Int. Cl.
*A61K 39/40* (2006.01)
*A61K 39/42* (2006.01)
*A61K 39/44* (2006.01)
*A61K 39/395* (2006.01)

(52) U.S. Cl. ............... 424/181.1; 424/178.1; 435/6; 435/91.1; 525/461

(58) Field of Classification Search ............ 424/181.1, 424/178.1; 435/6, 91.1; 536/24.2, 23.1; 540/474; 525/461
See application file for complete search history.

(56) References Cited

U.S. PATENT DOCUMENTS

| | | | |
|---|---|---|---|
| 3,268,550 A | 8/1966 | Heller | 260/315 |
| 4,014,987 A | 3/1977 | Heller et al. | 424/15 |
| 4,079,038 A | 3/1978 | Choi et al. | 260/47 XA |
| 4,093,709 A | 6/1978 | Choi et al. | 424/19 |
| 4,131,648 A | 12/1978 | Choi et al. | 424/22 |
| 4,131,662 A | 12/1978 | Cekoric et al. | 264/51 |
| 4,138,344 A | 2/1979 | Choi et al. | 252/1 |
| 4,180,064 A | 12/1979 | Heller et al. | 128/130 |
| 4,180,646 A | 12/1979 | Choi et al. | 528/153 |
| 4,249,531 A | 2/1981 | Heller et al. | 128/260 |
| 4,261,969 A | 4/1981 | Heller | 424/19 |
| 4,304,767 A | 12/1981 | Heller et al. | 424/78 |
| 4,502,976 A | 3/1985 | Heller | 252/315.4 |
| 4,513,143 A | 4/1985 | Ng et al. | 549/335 |
| 4,548,990 A | 10/1985 | Mueller et al. | 525/123 |
| 4,549,010 A | 10/1985 | Sparer et al. | 528/361 |
| 4,590,190 A | 5/1986 | Saito et al. | 514/221 |
| 4,605,670 A | 8/1986 | Saito et al. | 514/619 |
| 4,639,366 A | 1/1987 | Heller | 424/19 |
| 4,690,682 A | 9/1987 | Lim | 604/891 |
| 4,690,825 A | 9/1987 | Won | 424/501 |
| 4,710,497 A | 12/1987 | Heller et al. | 514/221 |
| 4,713,441 A * | 12/1987 | Heller et al. | 528/392 |
| 4,745,160 A | 5/1988 | Churchill et al. | 525/415 |
| 4,752,612 A | 6/1988 | Saito et al. | 514/420 |
| 4,764,364 A | 8/1988 | Heller et al. | 424/78 |
| 4,765,973 A * | 8/1988 | Heller | 424/486 |
| 4,801,457 A | 1/1989 | Heller et al. | 424/422 |
| 4,818,542 A | 4/1989 | DeLuca et al. | 424/491 |
| 4,849,426 A | 7/1989 | Pearlman | 514/274 |
| 4,855,132 A | 8/1989 | Heller et al. | 424/78 |
| 4,898,928 A * | 2/1990 | Heller et al. | 528/392 |
| 4,923,645 A | 5/1990 | Tsang et al. | 264/4.3 |
| 4,938,763 A | 7/1990 | Dunn et al. | 604/891.1 |
| 4,946,931 A | 8/1990 | Heller et al. | 528/230 |
| 4,957,998 A | 9/1990 | Heller et al. | 528/220 |
| 4,963,369 A | 10/1990 | Song et al. | 426/5 |
| 5,013,553 A | 5/1991 | Southard et al. | 424/426 |
| 5,013,821 A | 5/1991 | Heller et al. | 528/376 |
| 5,028,435 A | 7/1991 | Katz et al. | 424/484 |
| 5,030,457 A | 7/1991 | Ng et al. | 424/486 |
| 5,037,883 A | 8/1991 | Kopecek et al. | 525/54.1 |
| 5,047,464 A | 9/1991 | Pogany et al. | 524/500 |
| 5,077,049 A | 12/1991 | Dunn et al. | 424/426 |
| 5,108,755 A | 4/1992 | Daniels et al. | 424/426 |
| 5,128,376 A | 7/1992 | Saito et al. | 514/772 |
| 5,217,712 A | 6/1993 | Pogany et al. | 424/78.18 |
| 5,278,201 A | 1/1994 | Dunn et al. | 523/113 |
| 5,324,519 A | 6/1994 | Dunn et al. | 424/426 |
| 5,324,520 A | 6/1994 | Dunn et al. | 424/435 |
| 5,334,640 A | 8/1994 | Desai et al. | 524/56 |

(Continued)

FOREIGN PATENT DOCUMENTS

DE    0291668 A7    7/1991

(Continued)

OTHER PUBLICATIONS

K. Abdellaoui et al., "Metabolite-derived artificial polymers designed for drug targeting, cell penetration and bioresorption", *Eur J Pharm Sci*, 6. 61-73, 1998.

(Continued)

*Primary Examiner*—Vickie Kim
(74) *Attorney, Agent, or Firm*—Heller Ehrman LLP

(57) ABSTRACT

Degradable polyacetal polymers and functionalized degradable polyacetal polymers have properties favorable for use in pharmaceutical and biomedical applications. The degradable polyacetal polymers are relatively stable at physiological pH with favorable biodistribution profiles, and degrade readily in low pH conditions. Conjugates of the polymers with drugs, especially anticancer drugs, and methods of treatment of cancer.

7 Claims, 7 Drawing Sheets

U.S. PATENT DOCUMENTS

| | | | |
|---|---|---|---|
| 5,336,505 A | 8/1994 | Ng et al. | 424/486 |
| 5,340,849 A | 8/1994 | Dunn et al. | 523/113 |
| 5,368,859 A | 11/1994 | Dunn et al. | 424/426 |
| 5,407,609 A | 4/1995 | Tice et al. | 264/4.6 |
| 5,422,121 A | 6/1995 | Lehmann et al. | 424/464 |
| 5,449,670 A | 9/1995 | Skinner et al. | 514/3 |
| 5,461,140 A | 10/1995 | Heller et al. | 528/425 |
| 5,468,478 A | 11/1995 | Saifer et al. | 424/78.27 |
| 5,487,897 A | 1/1996 | Polson et al. | 424/426 |
| 5,505,966 A | 4/1996 | Edman et al. | 424/493 |
| 5,525,634 A | 6/1996 | Sintov et al. | 514/777 |
| 5,540,912 A | 7/1996 | Roorda et al. | 424/422 |
| 5,599,552 A | 2/1997 | Dunn et al. | 424/423 |
| 5,605,933 A | 2/1997 | Duffy et al. | 514/557 |
| 5,607,686 A | 3/1997 | Totakura et al. | 424/426 |
| 5,608,060 A * | 3/1997 | Axworthy et al. | 540/474 |
| 5,622,718 A | 4/1997 | Al-Shamkhani et al. | 424/488 |
| 5,627,187 A | 5/1997 | Katz | 514/274 |
| 5,632,727 A | 5/1997 | Tipton et al. | 602/47 |
| 5,660,849 A | 8/1997 | Polson et al. | 424/426 |
| 5,670,602 A | 9/1997 | Kohn et al. | 528/176 |
| 5,681,873 A | 10/1997 | Norton et al. | 523/115 |
| 5,700,804 A | 12/1997 | Collins et al. | 514/255 |
| 5,702,716 A | 12/1997 | Dunn et al. | 424/422 |
| 5,725,491 A | 3/1998 | Tipton et al. | 602/43 |
| 5,733,950 A | 3/1998 | Dunn et al. | 523/113 |
| 5,738,864 A | 4/1998 | Schacht et al. | 424/426 |
| 5,739,176 A | 4/1998 | Dunn et al. | 523/113 |
| 5,744,153 A | 4/1998 | Yewey et al. | 424/426 |
| 5,759,563 A | 6/1998 | Yewey et al. | 424/426 |
| 5,780,044 A | 7/1998 | Yewey et al. | 424/426 |
| 5,783,205 A | 7/1998 | Berggren et al. | 424/426 |
| 5,792,469 A | 8/1998 | Tipton et al. | 424/422 |
| 5,824,343 A | 10/1998 | Ng et al. | 424/486 |
| 5,837,228 A | 11/1998 | Shih et al. | 424/78.37 |
| 5,852,018 A | 12/1998 | Bryans et al. | 514/252 |
| 5,861,387 A * | 1/1999 | Labrie et al. | 514/169 |
| 5,861,400 A | 1/1999 | Brocchini et al. | 514/252 |
| 5,863,990 A * | 1/1999 | Papisov | 525/398 |
| 5,877,224 A | 3/1999 | Brocchini et al. | 514/772.2 |
| 5,891,877 A | 4/1999 | Brocchini et al. | 514/235.8 |
| 5,902,812 A | 5/1999 | Brocchini et al. | 514/253 |
| 5,916,597 A | 6/1999 | Lee et al. | 424/501 |
| 5,935,955 A | 8/1999 | Ashworth et al. | 514/235.8 |
| 5,939,453 A | 8/1999 | Heller et al. | 514/452 |
| 5,945,115 A | 8/1999 | Dunn et al. | 424/422 |
| 5,965,118 A | 10/1999 | Duncan et al. | 424/78.27 |
| 5,968,543 A | 10/1999 | Heller et al. | 424/425 |
| 5,985,916 A | 11/1999 | Duncan et al. | 514/492 |
| 5,990,194 A | 11/1999 | Dunn et al. | 523/113 |
| 5,993,856 A | 11/1999 | Ragavan et al. | 424/489 |
| 6,007,845 A | 12/1999 | Domb et al. | 424/501 |
| 6,048,736 A | 4/2000 | Kosak | 436/536 |
| 6,071,530 A | 6/2000 | Polson et al. | 424/426 |
| 6,083,521 A | 7/2000 | Acemoglu et al. | 424/422 |
| 6,096,344 A | 8/2000 | Liu et al. | 424/501 |
| 6,143,314 A | 11/2000 | Chandrashekar et al. | 424/426 |
| 6,159,491 A | 12/2000 | Durrani | 424/430 |
| 6,166,173 A | 12/2000 | Mao et al. | 528/398 |
| 6,193,991 B1 | 2/2001 | Shukla | 424/426 |
| 6,206,920 B1 | 3/2001 | Eliaz et al. | 623/16.11 |
| 6,217,895 B1 | 4/2001 | Guo et al. | 424/427 |
| 6,238,705 B1 | 5/2001 | Liu et al. | 424/501 |
| 6,245,345 B1 | 6/2001 | Swanborn et al. | 424/402 |
| 6,261,583 B1 | 7/2001 | Dunn et al. | 424/422 |
| 6,262,127 B1 | 7/2001 | Acemoglu et al. | 514/772.7 |
| 6,281,015 B1 | 8/2001 | Mooney et al. | 435/395 |
| 6,287,588 B1 | 9/2001 | Shih et al. | 424/426 |
| 6,331,311 B1 | 12/2001 | Brodbeck et al. | 424/425 |
| 6,338,843 B1 | 1/2002 | Duncan et al. | 424/78.18 |
| 6,372,205 B1 | 4/2002 | Duncan et al. | 424/78.17 |
| 6,372,245 B1 | 4/2002 | Bowman et al. | 424/427 |
| 6,395,293 B2 | 5/2002 | Polson et al. | 424/426 |
| RE37,795 E | 7/2002 | Kohn et al. | 528/176 |
| 6,524,606 B1 | 2/2003 | Ng et al. | 424/425 |
| 6,585,956 B2 | 7/2003 | Malik et al. | 424/28.17 |
| 6,590,059 B2 | 7/2003 | Ng et al. | 528/220 |
| 6,613,355 B2 | 9/2003 | Ng et al. | 424/462 |
| 6,822,086 B1 * | 11/2004 | Papisov | 536/24.2 |
| 2002/0019446 A1 | 2/2002 | Brocchini et al. | 514/772.2 |
| 2002/0037300 A1 | 3/2002 | Ng et al. | 424/401 |
| 2002/0054863 A1 | 5/2002 | Malik et al. | 424/78.26 |
| 2002/0082362 A1* | 6/2002 | Brocchini et al. | 525/461 |
| 2002/0090398 A1 | 7/2002 | Dunn et al. | 424/486 |
| 2002/0151668 A1 | 10/2002 | James et al. | 528/44 |
| 2002/0168336 A1 | 11/2002 | Ng et al. | 424/78.38 |
| 2002/0176844 A1 | 11/2002 | Ng et al. | 424/78.38 |
| 2003/0064050 A1 | 4/2003 | Malik et al. | 424/78.17 |
| 2003/0068384 A1 | 4/2003 | Brochini et al. | 424/501 |
| 2003/0077295 A1 | 4/2003 | Malik et al. | 424/400 |
| 2003/0130472 A1 | 7/2003 | Ng et al. | 528/73 |
| 2003/0138474 A1 | 7/2003 | Ng et al. | 424/425 |
| 2003/0152630 A1 | 8/2003 | Ng et al. | 424/486 |
| 2003/0211072 A1 | 11/2003 | Carreno-Gomez et al. | 424/78.17 |

FOREIGN PATENT DOCUMENTS

| | | |
|---|---|---|
| DE | 4415204 A1 | 11/1995 |
| EP | 0322392 A1 | 6/1989 |
| EP | 0419156 A2 | 3/1991 |
| EP | 0466566 A2 | 1/1992 |
| EP | 0485840 A2 | 5/1992 |
| EP | 0485840 A3 | 5/1992 |
| EP | 0 524 831 A | 1/1993 |
| EP | 0471036 B1 | 1/1996 |
| EP | 1 142 596 A | 10/2001 |
| FR | 2238477 A2 | 2/1975 |
| FR | 2352547 A2 | 12/1977 |
| GB | 1482663 | 8/1977 |
| GB | 1579490 | 11/1980 |
| WO | 9012605 A1 | 11/1990 |
| WO | 9013361 A1 | 11/1990 |
| WO | 9103510 A1 | 3/1991 |
| WO | 9115242 | 10/1991 |
| WO | 9200732 A1 | 1/1992 |
| WO | 9202210 A1 | 2/1992 |
| WO | 9300383 | 1/1993 |
| WO | 9404512 | 3/1994 |
| WO | 9404513 | 3/1994 |
| WO | 9407536 | 4/1994 |
| WO | 9414417 A1 | 7/1994 |
| WO | 9505200 | 2/1995 |
| WO | 9516659 A1 | 6/1995 |
| WO | 9521829 | 8/1995 |
| WO | 9521830 | 8/1995 |
| WO | 9521831 | 8/1995 |
| WO | 9521832 | 8/1995 |
| WO | 9620180 | 7/1996 |
| WO | 9620190 | 7/1996 |
| WO | 96/32419 A | 10/1996 |
| WO | 9630331 | 10/1996 |
| WO | 9704744 | 2/1997 |
| WO | 9725026 | 7/1997 |
| WO | 9725366 A1 | 7/1997 |
| WO | 9725980 A1 | 7/1997 |
| WO | 9847496 | 10/1998 |
| WO | 9847537 | 10/1998 |
| WO | 9856424 | 12/1998 |
| WO | 9856425 | 12/1998 |
| WO | 9952962 | 10/1999 |
| WO | 9962983 A1 | 12/1999 |
| WO | 0000159 A2 | 1/2000 |
| WO | 0078355 | 12/2000 |

| | | |
|---|---|---|
| WO | 0115734 A2 | 3/2001 |
| WO | 0118080 | 3/2001 |
| WO | 0135929 A2 | 5/2001 |
| WO | 0136002 | 5/2001 |
| WO | 0152896 | 7/2001 |
| WO | 0174411 A1 | 10/2001 |
| WO | 0185139 | 11/2001 |
| WO | 0185139 A2 | 11/2001 |
| WO | 0202146 | 1/2002 |
| WO | 0220663 | 3/2002 |
| WO | 0220663 A2 | 3/2002 |
| WO | 0245682 | 6/2002 |
| WO | 02092061 | 11/2002 |
| WO | 02092061 A1 | 11/2002 |
| WO | 02092655 | 11/2002 |
| WO | 02092655 A1 | 11/2002 |
| WO | 02092661 | 11/2002 |
| WO | 02092661 A2 | 11/2002 |
| WO | 03037383 | 5/2003 |
| WO | 03044076 | 5/2003 |
| WO | 03044446 A1 | 5/2003 |
| WO | 03089010 | 10/2003 |

OTHER PUBLICATIONS

V. Alakhov et al., "Block copolymeric biotransport carriers as versatile vehicles for drug delivery", *Exp Opin Invest Drugs,* 7(9), 1453-1473, 1998.

A. Al-Shamkhani et al., "Synthesis controlled release properties and antitumor activity of alginate cis-aconityl daunomycin conjugates", *Int J Pharm,* 122, 107-119, 1995.

A.E. Bolton et al., "The labeling of proteins to high specific radioactivities . . . " *Biochem. J,* 133, :529-38, 1973.

P. Balboni, et al., "Activity of albumin conjugates of 5-fluorodeoxyuridine and cytosine arabinoside on poxviruses as a lysosomotropic antiviral chemotherapy", *Nature,* 264, 181-183, 1976.

C. Delgado et al., "The uses and properties of PEG-liked proteins", *Crit. Rev. Ther. Drug Carrier Syst,* B, 249-304, 1992.

F. Dosio et al., "Preparation, characterization and properties in vitro and in vivo of a paclitaxel-albumin conjugate", *J. Cont. Rel.,* 47(3), 293-304, 1997.

R. Duncan, "Polymer therapeutics for tumor specific delivery", *Chem & Ind,* 7, 262-264, 1997.

R. Duncan, "Drug-polymer conjugates: potential for improved chemotherapy", *Anti-Cancer Drugs.* 3, 175-210, 1992.

R. Duncan et al., "The role of polymer conjugates in the diagnosis and treatment of cancer", *STP Pharma,* 6, 237-263, 1996.

E. Eno-Amooquaye et al., "Altered biodistribution of an antibody-enzyme conjugate modified with polyethylene glycol", *Br J Cancer,* 73, 1323-1327, 1996.

P. Flanagan et al., "Evaluation of antibody-[N-(2-hydroxypropyl)methacrylamide] copolymer conjugates as targetable drug-carriers. 2. Body distribution of anti Thy-1,2 antibody, anti-transferrin receptor antibody B3/25 and transferrin conjugates in DBA2 mice and activity of conjugates containing daunomycin against L1210 leukemia in vivo", *J Cont Rel,* 18, 25-38, 1992.

Greenfield et al., "Evaluation in vitro of adriamycin Immunoconjugates . . . ", *Cancer Res,* 50, 6600-6607 (1990).

D. Gaal et al., "Low toxicity and high antitumor activity of daunomycin by conjugation to an immunopotential amphoteric branched polypeptide", *Eur J Cancer,* 34(1), 155-16, 1998.

C. Hall et al., "Experimental hypertension elicited by injections methyl cellulose", *Experientia* 17, 544-454, 1961.

C. Hall et al., "Macromolecular hypertension: hypertensive cardiovascular disease from subcutaneously administered polyvinyl alcohol", *Experientia* 18, 38-40, 1962.

J. Heller et al., "Preparation of polyacetals by the reaction of divinyl ethers and polyols", *J Polym Sci: Polym Lett Ed,* 18, 293-297, 1980.

K. James et al., "Pseudo-poly(amino acid)s: Example for synthetic materials derived from natural metabolites", in: K. Park, ed., Controlled Drug Delivery: Challenges and Strategies, Washington, DC: *American Chemical Society,* 389-403, 1997.

G. Kwon et al., Block copolymer micelles as long-circulating drug vehicles, *Adv Drug Del Rev,* 16, 295-309, 1995.

C. Monfardini et al., "Stabilization of substances in circulation", *Bioconjugate Chem,* 9, 418-450, 1998.

S. Morgan et al., "Alginates as drug carriers: covalent attachment of alginates to therapeutic agents containing primary amine groups", *In. J Pharm,* 122, 121-128, 1995.

A. Nathan et al., Copolymers of lysine and polyethylene glycol: A new family of functionalized drug carriers, *Bioconjugate Chem* 4, 54-62, 1993.

H. Nogusa et al., "Synthesis of carboxymethylpullulan peptide doxorubicin conjugates and their properties", *Chem Pharm Bull,* 43, 1931-1936, 1995.

M.L. Nucci et al., "The therapeutic values of poly(ethylene glycol)-modified proteins", *Adv Drug Delivery Rev* 6, 133-151, 1991.

Y. Ohya et al., "I-1,4-Polygalactosamine immobilised 5-fluorouracils through hexamethylene spacer groups via urea bonds", *J Cont Rel,* 17, 259-266, 1991.

Y. Ohya et al., "In vivo and in vitro antitumor activity of CM-Chitin immobilized doxorubicins by lysosomal digestible tetrapeptide spacer groups", *J Bioact Compat Polymers,* 10, 223-234, 1995.

T. Ouchi et al., "Synthesis and antitumor activity of conjugates of poly (a-malic acid) and 5-fluorouracil bound via ester, amide or carbamoyl bonds", *J Cont Rel,* 12, 143-153, 1990.

D. Putnam et al., "Polymer conjugates with anticancer activity", *Adv Polym Sci,* 122, 55-123, 1995.

B. Schechter et al., "Soluble polymers as carriers of cisplatinum", *J Cont Rel,* 10, 75-87, 1989.

P. Schneider et al., "A review of drug-induced lysosomal disorders of the liver in man and laboratory animals", *Microscopy Res Tech* 36, 253-275, 1997.

L. Seymour et al., "Effect of molecular weight (Mw) of N-(2-hydroxypropyl)methacrylamide copolymers on body distributions and rate of excretion after subcutaneous, intraperitoneal and intravenous administration to rats", *J. Biomed Mater Res* 21, 341-1358, 1987.

W. Shalaby et al., "Chemical modification of proteins and polysaccharides and its effect on enzyme-catalyzed degradation", in: S. Shalaby, ed. Biomedical Polymers. *Designed-to-degrade systems.* New York: Hanser Publishers, 1994.

C. Springer et al., "Ablation of human choriocarcinoma xenografts in nude mice by antibody-directed enzyme prodrug therapy (ADEPT) with three novel compounds", *Eur J Cancer,* 11, 1362-1366, 1991.

T. Tanaka et al., "Intracellular disposition and cytotoxicity of transferrin-mitomycin C conjugate in HL60 cells as a receptor-mediated drug targeting system", *Biol Pharm Bull,* 21(2), 147-152, 1998.

L. Torres et al., "A new polymerization system for bicyclic acetals: Toward the controlled/"living" cationic ring-opening polymerization of 6,8-dioxabicyclo[3.2.1] octane", *Macromolecules,* 32, 6958-6962, 1999.

P. Trail et al., "Site-directed delivery of anthracyclines for the treatment of cancer", *Drug Dev Res* 34, 196-209, 1995.

A. Trouet et al., "A covalent linkage between daunorubicin and proteins that is stable in serum and reversible by lysosomal hydrolases as required for a lysosomotropic drug-carrier conjugate. In vitro and in vivo studies", *Proc. Natl. Acad. Sci.* USA, 79, 626-629, 1982.

P. Vasey et al., "Phase 1 clinical and pharmacokinetic study of PKI (HPMA copolymer doxorubicin): first member a new class of chemotherapeutic agents: drug-polymer conjugates" *Clin Cancer Res,* 5, 83-94. 1999.

J. Vercauteren et al., "Effect of the chemical modification of dextran on the degration by dextranases", *J Bio Comp Polymers* 5, 4-15, 1990.

A. Wunder et al., "Antitumor activity of methotrexate-albumin conjugates in rats bearing a Walker-256 carcinoma", *Int J Cancer,* 76, 884-890, 1998.

T. Yasuzawa et al, "Structural determination of the conjugate of human serum albumin with a mitomycin C derivative, KW-2149, by matrix assisted laser desorption/ionization mass spectrometry", *Bioconjugate Chem*, 8, 391-399, 1997

S. Zalipsky, "Chemistry of polyethylene glycol conjugates with biologically active molecules", *Adv Drug Delivery Rev*, 16, 157-182, 1995.

Andriano et al., "Preliminary effects of in vitro lipid exposure on absorbably poly(ortho ester) films," *J Appl Biomater.* 6(2):129-35 (1995).

Ashford et al., "An evaluation of pectin as a carrier for drug targeting to the colon," *Chemical Abstracts* 119:278554r (1993) pp. 514.

Bart et al. "Post surgical pain management with poly(ortho esters)," *Adv Drug Deliv Rev.* 54(7):1041-8 (2002).

Bernatchez et al. "Biotolerance of a semisolid hydrophobic biodegradable poly(ortho ester) for controlled drug delivery," *J Biomed Mater Res.* 27(5):667-81 (1993).

Castillo et al. "*Glucocorticoids Prolong Rat Sciatic Nerve Blockade In Vivo from Bupivacine Microspheres,*" *Anesthesiology* 85(3):1157-1166 (1996).

Chia et al. "Auto-catalyzed poly(ortho ester) microspheres: a study of their erosion and drug release mechanism," *J Control Release,* 75(1-2): 11-25 (2001).

*Contemporary Polymer Chemistry 3rd Ed.* Allcock et al. (*eds.*) *Upper Saddle River, New Jersey: Pearson Education, Inc.* Ch. 1 pp. 11-12 (2003).

Dahl JB et al. "Wound inflation with local anaesthetics for postoperative pain relief," *Acta Anaesthesiol Scand* 38: 7-14 (1994).

Derwent Abstract, Accession No. 10473386 for German Patent Application DE 4415204 published Nov. 2, 1995, "Compsns contg retinyl salicylate or acetyl-salicylate—for pharmaceutical or cosmetic treatment of inflammation, general necrosis, intoxication, allergies, tumours, etc.".

Derwent Abstract, Accession No. 15388893 for PCT Patent Publication WO 200344446 published May 30, 2003, "Disposal of materials containing high-energy substances, especially shells, comprises recycling bulk material leaving a fluidized bed in a non-cooled state to a different inlet region than the materials for disposal".

Derwent Abstract, Accession No. 8850667 for German Patent Application DD 291668 A published Jul. 11, 1991, "GnRH prepn. for oral use—consist of GNRH nucleus contg. detergent to promote resorption, inner coating which dissolves in the colon and outer coating".

Deshpande et al. "Bioerodible polymers for ocular drug delivery," *Crit Rev Ther Drug Carrier Syst.* 15(4):381-420 (1998).

Dräger et al., "Prolonged Intercostal Nerve Blockade in Sheep Using Controlled-release of Bupivacaine and Dexamethasone for Polymer Microspheres," *Anesthesiology* 89(4):969-979 (1998).

Duenas et al., "Sustained Delivery of rhVEGF from a Novel injectable Liquid, PLAD," *Proceed Int'l Symp. Control Rel. Bioact. Mater.* 28:1041-1042 (2001).

Einmahl et al., "A viscous bioerodible poly(ortho ester) as a new biomaterial for intraocular application," *J Biomed Mater Res.* 50(4):566-73 (2000).

Einmahl et al., "Concomitant and controlled release of dexamethasone and 5-fluorouracil from poly(ortho ester)," *Int J Pharm.* 185(2):189-98 (1999).

Geary RS et al. "Vancomycin and insulin used as models for oral delivery of peptides," *J of Controlled Release* 23:65-74 (1993).

Heller et al., "Controlled drug release from bioerodible hydrophobic ointment," *Biomaterials,* 11(4):235-7 (1990).

Heller et al., "Controlled release of water-soluble macromolecules from bioerodible hydrogels," *Biomaterials,* 4(4):262-6 (1983).

Heller J et al "Controlled Drug release by polymer dissolution. II: Enzyme-mediated delivery device," *J Pharm Sci.* 68(7):919-21 (1979).

Heller et al., "Poly(ortho ester) biodegradable polymer systems," *Methods Enzymol.* 112:422-36 (1985).

Heller et al. "Controlled release of contraceptive steroids from biodegradable poly (ortho esters)," *Contracept Deliv Syst.* 4(1):43-53 (1983).

Heller et al. "Poly(ortho esters)—their development and some recent applications," *Eur J Pharm Biopharm.* 50(1):121-8. (2000) Review. Erratum in: Eur J Biopharm Sep. 2000;50(2):327.

Heller et al. "Development and applications injectable poly(ortho esters) for pain control and periodontal treatment," *Biomaterials* 23(22):4397-404 (2002).

Heller J., "Controlled drug release from poly(ortho esters)," *Ann N Y Acad Sci.* 446:51-66 (1985).

Heller J., "Modulated release from drug delivery devices," *Crit Rev Ther Drug Carrier Syst.* 10(3):253-305 (1993).

Heller et al. "Poly(ortho esters): synthesis, characterization, properties and uses," *Adv Drug Deliv Rev.* 54(7):1015-39 (2002).

Heller J., "Controlled release of biologically active compounds from bioerodible polymers," *Biomaterials,* 1(1):51-7 (1980).

Heller J., "The use of polymers in the construction of controlled-release devices," *NIDA Res Monogr.* 154:107-31 (1995).

Heller J., "Biodegradable polymers in controlled drug delivery," *Crit Rev Ther Drug Carrier Syst.* 1(1):39-90 (1993).

Leadley et al., "The use of SIMS, XPS and in situ AFM to probe the acid catalysed hydrolysis of poly(orthoesters)," *Biomaterials.* 19(15):1353-60 (1998).

Merkli et al., "Synthesis and characterization of a new biodegradable semi-solid poly(ortho ester) for drug delivery systems," *Biomater Sci Polym Ed.* 4(5):505-16 (1993).

Merkli et al., "Gamma sterilization of a semi-solid poly(ortho ester) designed for controlled drug delivery—validation and radiation effects," *Pharm Res.* 11(10):1485-91 (1994).

Merkli et al., "Purity and stability assessment of a semi-solid poly(ortho ester) used in drug delivery systems," *Biomaterials,* 17(9):897-902 (1996).

Milojevic S et al. "Amylose as a coating for drug delivery to the colon: preparation and vitro evaluation using 5-aminosalicylic acid pellets," *J of Controlled Release* 38:75-84 (1996).

Ng et al., "Development of a poly(ortho ester) prototype with a latent acid in the polymer backbone for 5-fluorouracil delivery," *J. Control Release* 65:367-74 (2000).

Ng et al., "Controlled drug release from self-catalyzed poly(ortho esters)," *Ann N Y Acad Sci.* 831: 168-78 (1997).

Okumu et al., "Sustained Delivery of Growth Hormone from a Novel Injectable Liquid, PLAD," *Proceed. Int'l Symp. Control Rel. Bioact. Mater.* 28:1029-1030 (2001).

Press Release: "Advanced Polymer Systems Granted Two Composition of Matter Patents Related to its Bioerodible Polymer Technology," Advanced Polymer Systems News Release, Oct. 1999.

Roskos et al., "Development of a drug delivery system for the treatment of periodontal disease based on bioerodible poly(ortho esters)," *Biomaterials.* 16(4):313-7

Rothen-Weinhold et al., "Release of BSA from poly(ortho ester) extruded thin strands," *J Control Release,* 71(1):31-7 (2001).

Schwach-Abdellaoui et al., "Optimization of novel bioerodible device based on auto-catalyzed poly(ortho esters) for controlled delivery of tetracycline to periodontal pocket," *Biomaterials.* 22(12):1659-66 (2001).

Schwach-Abdellaoui et al., "Bioerodible injectable poly(ortho ester) for tetracycline controlled delivery to periodontal pockets: preliminary trial in humans," *AAPS PharmSci.* 4(4):artcle 20 pp. 1-7 (2002).

Schwach-Abdellaoui et al., "Synthesis and characterization of self-catalyzed poly(ortho-esters) based on decanediol and decanediol-lactate," *J Biomater Sci Polym Ed.* 10(3):375-89 (1999).

Shi et al., "Double walled POE/PLGA microspheres: encapsulation of water-soluble and water-insoluble proteins and their release properties," *J Control Release,* 89(2):167-77 (2003).

Sintzel et al., "In vitro drug release from self-catalyzed poly(ortho ester): case study of 5-fluorouracil," *J Control Release.* 55(2-3):213-8 (1998).

Sintzel et al., "Synthesis and characterization of self-catalyzed poly(ortho ester)," *Biomaterials.* 19(7-9):791-800 (1998).

Steinicke A. et al. "Oral formulations of gonadotropin releasing hormone" *Chemical Abstracts* 115(22):239759j (1991).

Taylor et al., "Six bioabsorbable polymers: in vitro acute toxicity of accumulated degradation products," *J Appl Biomater.* 5(2):151-7 (1994).

*Textbook of Polymer Science 3rd Ed.* Billmeyer, F.W. (ed.) New York: John Wiley & Sons Ch. 17 pp. 457-485 (1984).

Uyeda, C.T., "Agglutination of Cardiolipin-Coated Latex Particles with VDRL- And Kolmer-Positive Serums," *American Journal of Clinical Pathology* 40:329-333 (1963).

van de Weert et al., "Semi-sold self-catalyzed poly(ortho ester)s as controlled-release systems: protein release and protein stability issues," *J Pharm Sci.* 91(4):1065-74 (2002).

Wan et al., "POE-PEG-POE triblock copolymeric microspheres containing protein. II. Polymer erosion and protein release mechanism," *J Control Release.* 75(1-2):129-41 (2001).

Yang et al. "POE/PLGA composite microspheres: formation and in vitro behavior of double walled microspheres," *J Control Release.* 88(2):201-13 (2003).

Yang et al. "POE-PEG-POE triblock copolymeric microspheres containing protein. I. Preparation and characterization," *J Control Release.* 75(1-2):115-28 (2001).

Zignani et al., "A poly(ortho ester) designed for combined ocular delivery of dexamethasone sodium phosphate and 5-fluorouracil: subconjunctival tolerance and in vitro release," *Eur J Pharm Biopharm.* 50(2):251-5 (2000).

Zignani et al., "Improved biocompatibility of a viscous bioerodible poly(ortho ester) by controlling the environmental pH during degradation," *Biomaterials* 21(17):1773-8 (2000).

* cited by examiner

DEGRADABLE POLYACETAL POLYMERS

CROSS-REFERENCE TO RELATED APPLICATION

This invention claims the priority under 35 USC 119(e) of Provisional Application No. 60/230,377, filed Sep. 6, 2000, the disclosure of which is incorporated herein by reference.

BACKGROUND TO THE INVENTION

1. Field of the Invention

This invention relates to degradable polyacetal polymers and therapeutic agents derived therefrom, the production of these materials, and methods of disease treatment using them.

2. Description of the Related Art

Polymer therapeutics (R. Duncan, "Polymer therapeutics for tumor specific delivery", Chem. & Ind., 7, 262–264, 1997) are developed for biomedical applications requiring physiologically soluble polymers; and include biologically active polymers, polymer-drug conjugates, polymer-protein conjugates, and other covalent constructs of bioactive molecules. An exemplary class of a polymer-drug conjugate is derived from copolymers of hydroxypropyl methacrylamide (HPMA), which have been extensively studied for the conjugation of cytotoxic drugs for cancer chemotherapy (R. Duncan, "Drug-polymer conjugates: potential for improved chemotherapy", Anti-Cancer Drugs, 3, 175–210, 1992; D. Putnam et al., "Polymer conjugates with anticancer activity", Adv. Polym. Sci., 122, 55–123, 1995; R. Duncan et al., "The role of polymer conjugates in the diagnosis and treatment of cancer", STP Pharma, 6, 237–263, 1996). An HPMA copolymer conjugated to doxorubicin, known as PK-1, is currently in Phase II evaluation in the UK. PK-1 displayed reduced toxicity compared to free doxorubicin in the Phase I studies (P. Vasey et al., "Phase I clinical and pharmacokinetic study of PKI (HPMA copolymer doxorubicin): first member of a new class of chemotherapeutic agents: drug-polymer conjugates" Clin. Cancer Res., 5, 83–94. 1999). The maximum tolerated dose of PK-1 was 320 mg/m$^2$, which is 4–5 times higher than the usual clinical dose of free doxorubicin.

The polymers used to develop polymer therapeutics may also be separately developed for other biomedical applications that require the polymer be used as a material. Thus, drug release matrices (including microparticles and nanoparticles), hydrogels (including injectable gels and viscous solutions) and hybrid systems (e.g. liposomes with conjugated poly(ethylene glycol) on the outer surface) and devices (including rods, pellets, capsules, films, gels) can be fabricated for tissue or site specific drug delivery. Polymers are also clinically widely used as excipients in drug formulation. Within these three broad application areas: (1) physiologically soluble molecules, (2) materials, and (3) excipients, biomedical polymers provide a broad technology platform for optimizing the efficacy of an active therapeutic drug.

An increasing number of physiologically soluble polymers have been used as macromolecular partners for the conjugation of bioactive molecules. Many polymers have the disadvantage of being non-degradable in the polymer backbone. For example, poly(ethylene glycol) (C. Monfardini et al., "Stabilization of substances in circulation", Bioconjugate Chem., 9, 418–450, 1998; S. Zalipsky, "Chemistry of polyethylene glycol conjugates with biologically active molecules", Adv. Drug Delivery Rev, 16, 157–182, 1995; C. Delgado et al., "The uses and properties of PEG-liked proteins", Crit. Rev. Ther. Drug Carrier Syst., B, 249–304, 1992; M. L. Nucci et al., "The therapeutic values of poly(ethylene glycol)-modified proteins", Adv. Drug Delivery Rev. 6, 133–151, 1991; A. Nathan et al., Copolymers of lysine and polyethylene glycol: A new family of functionalized drug carriers", Bioconjugate Chem. 4, 54–62, 1993) and HPMA (D. Putnam et al., "Polymer conjugates with anticancer activity", Adv. Polym. Sci., 122, 55–123, 1995; and R. Duncan et al., "The role of polymer conjugates in the diagnosis and treatment of cancer", STP Pharma, 6, 237–263, 1996) copolymers have been extensively studied for conjugation. PEG is also generally used in the pharmaceutical industry as a formulation excipient. These hydrophilic polymers are soluble in physiological media, but their main disadvantage is that the polymer mainchain does not degrade in vivo. Thus it is not possible to prohibit accumulation of these polymers in the body. Only polymers with a molecular weight lower than the renal threshold can be used for systemic administration. It is imperative that for the systemic use of non-degradable polymers such as BPMA and PEG only molecules of a molecular weight which are readily cleared be administered or else long-term deleterious accumulation in healthy tissue will invariably result (L. Seymour et al., "Effect of molecular weight (Mw) of N-(2-hydroxypropyl)methacrylamide copolymers on body distributions and rate of excretion after subcutaneous, intraperitoneal and intravenous administration to rats", J. Biomed. Mater. Res. 21, 341–1358, 1987; P. Schneider et al., "A review of drug-induced lysosomal disorders of the liver in man and laboratory animals", Microscopy Res. Tech. 36, 253–275, 1997; C. Hall et al., "Experimental hypertension elicited by injections of methyl cellulose", Experientia 17, 544–454, 1961; C. Hall et al., "Macromolecular hypertension: hypertensive cardiovascular disease from subcutaneously administered polyvinyl alcohol", Experientia 18, 38–40, 1962).

Although some natural polymers such as polysaccharides have the advantage of being degradable in vivo, e.g. dextran, they typically lack a strict structural uniformity and have the propensity upon chemical modification (i.e. conjugation of a bioactive molecule) to become immunogenic or non-degradable (J. Vercauteren et al., "Effect of the chemical modification of dextran on the degradation by dextranases", J. Bio. Comp. Polymers 5, 4–15, 1990; W. Shalaby et al., "Chemical modification of proteins and polysaccharides and its effect on enzyme-catalyzed degradation", in: S. Shalaby, ed. Biomedical Polymers. Designed-to-degrade systems. New York: Hanser Publishers, 1994). Other polysaccharides which have been investigated for biomedical conjugation applications include chitosan (Y. Ohya et al., "α-1,4-Polygalactosamine immobilised 5-fluorouracils through hexamethylene spacer groups via urea bonds", J. Cont. Rel., 17, 259–266, 1991), alginate (A. Al-Shamkhani et al., "Synthesis, controlled release properties and antitumor activity of alginate cis-aconityl daunomycin conjugates", Int. J. Pharm., 122, 107–119, 1995; S. Morgan et al., "Alginates as drug carriers: covalent attachment of alginates to therapeutic agents containing primary amine groups", Int. J. Pharm., 122, 121–128, 1995), hyaluronic acid (B. Schechter et al., "Soluble polymers as carriers of cisplatinum", J. Cont. Rel., 10, 75–87, 1989), 6-O-carboxymethyl chitan (Y. Ohya et al., "In vivo and in vitro antitumor activity of CM-Chitin immobilized doxorubicins by lysosomal digestible tetrapeptide spacer groups", J. Bioact. Compat. Polymers, 10, 223–234, 1995) and 6-O-carboxymethyl pullulan (H.

Nogusa et al., "Synthesis of carboxymethylpullulan peptide doxorubicin conjugates and their properties", *Chem. Pharm. Bull.*, 43, 1931–1936, 1995).

Other natural polymers such as proteins can also be used to conjugate a bioactive molecule. For example albumin has been investigated as a protein used to conjugate a bioactive molecule (P. Balboni et al., "Activity of albumin conjugates of 5-fluorodeoxyuridine and cytosine arabinoside on poxyiruses as a lysosomotropic antiviral chemotherapy", *Nature*, 264, 181–183, 1976; A. Trouet et al., "A covalent linkage between daunorubicin and proteins that is stable in serum and reversible by lysosomal hydrolases as required for a lysosomotropic drug-carrier conjugate. In vitro and in vivo studies", *Proc. Natl. Acad. Sci. USA*, 79, 626–629, 1982; F. Dosio et al., "Preparation, characterization and properties in vitro and in vivo of a paclitaxel-albumin conjugate", *J. Cont. Rel.*, 47(3), 293–304, 1997; T. Yasuzawa et al, "Structural determination of the conjugate of human serum albumin with a mitomycin C derivative, KW-2149, by matrix assisted laser desorption/ionization mass spectrometry", *Bioconjugate Chem.*, 8, 391–399, 1997; A. Wunder et al., "Antitumor activity of methotrexate-albumin conjugates in rats bearing a Walker-256 carcinoma", *Int. J. Cancer*, 76, 884–890, 1998). The major limitations for using a protein to conjugate a bioactive compound include the propensity for inducing immunogenicity and non-specific degradation of the protein in vivo, and denaturation and irreversible alteration of the protein during preparation of the conjugate. Other proteins such as transferrin, which binds to the transferrin receptor and thus have the potential to undergo receptor-mediated uptake (T. Tanaka et al., "Intracellular disposition and cytotoxicity of transferrin-mitomycin C conjugate in HL60 cells as a receptor-mediated drug targeting system", *Biol. Pharm. Bull*, 21(2), 147–152, 1998) and various immuno-conjugates (D. Gaal et al., "Low toxicity and high antitumor activity of daunomycin by conjugation to an immunopotential ampho- teric branched polypeptide", *Eur. J. Cancer*, 34(1), 155–16, 1998; P. Trail et al., "Site-directed delivery of anthracyclines for the treatment of cancer", *Drug Dev. Res.* 34, 196–209, 1995; E. Eno-Amooquaye et al., "Altered biodistribution of an antibody—enzyme conjugate modified with polyethylene glycol", *Br. J. Cancer*, 73, 1323–1327, 1996; P. Flanagan et al., "Evaluation of antibody-[N-(2-hydroxypropyl)methacrylamide] copolymer conjugates as targetable drug-carriers. 2. Body distribution of anti Thy-1,2 antibody, anti-transferrin receptor antibody B3/25 and transferrin conjugates in DBA2 mice and activity of conjugates containing daunomycin against L1210 leukemia in vivo", *J. Cont. Rel.*, 18, 25–38, 1992; C. Springer et al., "Ablation of human choriocarcinoma xenografts in nude mice by antibody-directed enzyme prodrug therapy (ADEPT) with three novel compounds", *Eur. J. Cancer*, 11, 1362–1366, 1991.) also have been investigated. Monodisperse molecular weight distribution is often claimed to be a significant advantage for using proteins to conjugate drugs, but this can only be useful if a single species of the protein-drug conjugate can be reproducibly prepared on adequate scale which stable on storage. This is generally not economically or technologically possible to achieve in practice. Thus, there is a need for degradable synthetic polymers developed for biomedical application, and specifically for conjugation applications, which can address the limitations inherent in the use of natural polymers for these applications.

Synthetic polymers which have been prepared and studied that are potentially degradable include polymers derived from amino acids (e.g. poly(glutamic acid), poly[$^5$N-(2-hydroxyethyl)-L-glutamine), β-poly(2-hydroxyethyl aspartamide), poly(L-glutamic acid) and polylysine). These polymers when prepared for conjugation applications that require physiological solubility do not degrade in vivo to any extent within a time period of 10–100 hours. Additionally polymers and copolymers including pseudo-poly(amino acids) (K. James et al., "Pseudo-poly(amino acid)s: Examples for synthetic materials derived from natural metabolites", in: K. Park, ed., *Controlled Drug Delivery: Challenges and Strategies*, Washington, D.C.: American Chemical Society, 389–403, 1997) and polyesters such as copolymers of polylactic and poly(glycolic acid), poly(a or b-malic acid) (K. Abdellaoui et al., "Metabolite-derived artificial polymers designed for drug targeting, cell penetration and bioresorption", *Eur. J. Pharm. Sci.*, 6, 61–73, 1998; T. Ouchi et al., "Synthesis and antitumor activity of conjugates of poly (a-malic acid) and 5-fluorouracil bound via ester, amide or carbamoyl bonds", *J. Cont. Rel*, 12, 143–153, 1990), and block copolymers such as PEG-lysine (A. Nathan et al., "Copolymers of lysine and polyethylene glycol: A new family of functionalized drug carriers", *Bioconjugate Chem.*, 4, 54–62, 1993.), poly(lysine citramide) (K. Abdellaoui et al, "Metabolite-derived artificial polymers designed for drug targeting, cell penetration and bioresorption", *Eur. J. Pharm. Sci.*, 6, 61–73, 1998) and amino acid-PEG derived block copolymers (G. Kwon et al., Block copolymer micelles as long-circulating drug vehicles", *Adv. Drug Del. Rev.*, 16, 295–309, 1995; and V. Alakhov et al., "Block copolymeric biotransport carriers as versatile vehicles for drug delivery", *Exp. Opin. Invest. Drugs*, 7(9), 1453–1473, 1998) have also been investigated for conjugation.

Acetals are well known to be hydrolytically labile under mildly acidic conditions. Thus, biomedical polymers possessing acetal linkages in the polymer mainchain may undergo enhanced rates of hydrolysis in biological environments that are mildly acidic compared to biological environments that are at neutral or basic pH. For example, soluble polyacetals that can conjugate a bioactive molecule are expected to degrade at enhanced rates at the acetal functionality during cellular uptake because of the increase in acidity during endocytosis. Polyacetals will also display enhanced rates of hydrolysis in acidic regions of the gastrointestinal tract. Additionally polyacetals would be expected to degrade at enhanced rates at sites of diseased tissue that are mildly acidic (e.g. solid tumors).

Preparing polyacetals can be accomplished by acetal- or transacetalization reactions which result in the formation of a low molecular weight by-product (e.g. water or an alcohol). Complete removal of such a by-product is necessary for reproducible polymerization and to ensure the polyacetal does not degrade on storage. Usually harsh conditions are required to obtain high molecular weight polymer. If functionalized monomers relevant for biomedical applications are used, such conditions can often lead to unspecified chemical changes in the monomer. Polyacetals can be prepared without generation of a small molecule which requires removal by cationic ring-opening polymerization using bicyclic acetals (L. Torres et al., "A new polymerization system for bicyclic acetals: Toward the controlled/"living" cationic ring-opening polymerization of 6,8-dioxabicyclo [3.2.1] octane", *Macromolecules*, 32, 6958–6962, 1999). These reaction conditions lack versatility because they require bicyclic acetal monomers that are difficult to prepare with a wide range of chemical functionality useful for conjugation applications.

Polyacetals can also be prepared without generation of a small molecule byproduct that requires removal by the reaction of diols and di-vinyl ethers using an acid catalyst, as described by Heller (J. Heller et al., "Preparation of polyacetals by the reaction of divinyl ethers and polyols", *J. Polym. Sci.: Polym. Lett. Ed.*, 18, 293–297, 1980; J. Heller et al., "Polyacetal hydrogels formed from divinyl ethers and polyols", U.S. Pat. No. 4,713,441, 1987). Such polyacetals have uniform structure in that they are strictly alternating polymers of the A-B type. Uniform structure in biomedical polymer development is critical for optimization of the biological profile and to ensure the polymer meet regulatory requirements. The polymerization of diols and di-vinyl ethers occurs without the elimination of a small molecule under mild conditions. This is more efficient than polymerizations where there is a molecule (e.g. water or methanol) which must be removed. Polyacetals suitable for conjugation can be prepared by utilization of suitably functionalized diols, di-vinyl ethers, and/or hydroxy-vinyl ether monomers. Thus it becomes possible to prepare polyacetals for conjugation that possess conjugation functionality on either the A or B monomeric unit. Such structural uniformity is advantageous for controlling conjugation of bioactive molecules along the polymer mainchain.

The production of biodegradable polyacetals derived from polysaccharides which chemically has been described in WO 96/32419. This approach does not give polymeric materials displaying structural uniformity and suffers from the aforementioned limitations where chemical modification (i.e. conjugation of a bioactive molecule) often leads to the polysaccharide to become immunogenic or non-degradable. It is not possible to prepare polymeric materials displaying an alternating A-B structure, rather the structure of these polysaccharide derived polyacetals are too diverse to chemically analyze to the degree necessary to fulfill regulatory requirements.

The disclosures of these and other documents referred to throughout this application are incorporated herein by reference in their entirety.

SUMMARY OF THE INVENTION

The first aspect of the present invention relates to a class of new degradable polymers represented by Formula (I):

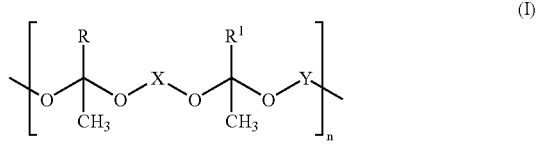

wherein R and $R^1$ are independently selected from the group consisting of hydrogen, $C_{1-18}$ alkyl, $C_{2-18}$ alkenyl, $C_{2-18}$ alkynyl, $C_{6-18}$ aryl, $C_{7-18}$ alkaryl and $C_{7-18}$ aralkyl groups;

X is a group capable of being covalently conjugated to a bioactive agent via a peptidic or a hydrolytically-labile bond;

Y is a group selected from the group consisting of $C_{1-200}$ alkanediyl, $C_{2-200}$ alkenediyl, $C_{2-200}$ alkynediyl, $C_{6-200}$ cycloalkanediyl, $C_{6-200}$ cycloalkenediyl, $C_{6-200}$ cycloalkynediyl, $C_{6-200}$ arylenediyl, $C_{6-200}$ alkarylenediyl, $C_{6-200}$ aralkylenediyl groups, or any of the above groups wherein the carbon backbone is substituted with one or more oxygen atoms within the carbon backbone; and n is an integer of 2–10,000.

Another aspect of the invention relates to a bioactive agent, preferably a drug, conjugated to a degradable polymer of Formula (I).

Another aspect of the invention relates to the preparation of the new degradable polymers and new polymer therapeutics.

A further aspect of the invention relates to a pharmaceutical composition comprising a therapeutically effective amount of a polymer-drug conjugate of the present invention in combination with one or more pharmaceutically acceptable carriers.

A further aspect of the invention relates to a method of treatment for diseases such as cancer, comprising administering to a patient in need of such treatment a therapeutically effective amount of a polymer therapeutic of the present invention.

Yet a further aspect of the present invention relates to prepolymers useful for the preparation of the degradable polymers.

DETAILED DESCRIPTION OF THE INVENTION

I. Definitions

Figure 1:
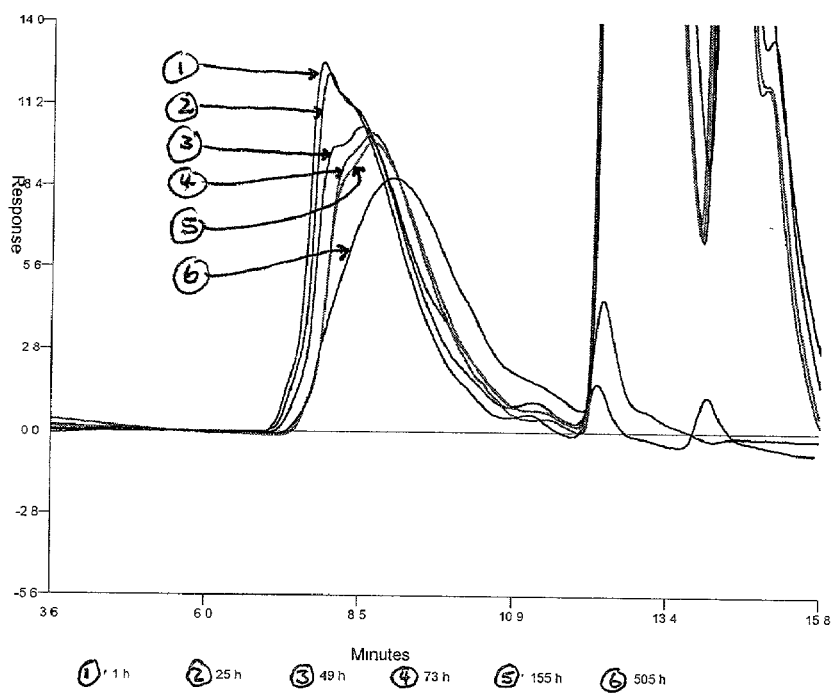
FIG. 1 is a graph showing the superposition of gel permeation chromatography traces for polyacetal 3 dissolved in solution at pH 7 and at 37° C. over a period of 21 days.

Terms used herein are based upon their recognized meanings and should be clearly understood by those skilled in the art.

The term "alkyl" refers to a straight or branched saturated monovalent hydrocarbon radical having the number of carbon atoms as indicated.

The term "alkenyl" refers to a straight or branched unsaturated monovalent hydrocarbon radical having the number of carbon atoms as indicated and the distinguishing feature of a carbon-carbon double bond.

The term "alkynyl" refers to a straight or branched unsaturated monovalent hydrocarbon radical having the number of carbon atoms as indicated and the distinguishing feature of a carbon-carbon triple bond.

The term "cycloalkyl" refers to a cyclic saturated monovalent hydrocarbon radical having the number of carbon atoms as indicated.

The terms "cycloalkenyl" and "cycloalkynyl" refer to cyclic unsaturated monovalent hydrocarbon radicals. A "cycloalkenyl" is characterized by a carbon-carbon double bond and a "cycloalkynyl" is characterized by a carbon-carbon triple bond.

The term "aryl" refers to a monovalent unsaturated aromatic carbocyclic radical having one or two rings, such as phenyl, naphthyl, indanyl or biphenyl, or to a monovalent unsaturated aromatic heterocyclic radical such as quinolyl, dihydroisoxazolyl, furanyl, imidazolyl, pyridyl, phthalimido, thienyl and the like.

The term "alkaryl" refers to an aryl group substituted with one or more alkyl groups.

The term "aralkyl" refers to an alkyl group substituted with one or more aryl groups.

The term "alkanediyl" refers to a straight or branched saturated divalent hydrocarbon radical having the number of carbon atoms indicated.

The terms "alkenediyl" and "alkynediyl" refer to straight or branched unsaturated divalent hydrocarbon radicals. An "alkenediyl" is characterized by a carbon-carbon double bond and an "alkynediyl" is characterized by a carbon-carbon triple bond.

The term "cycloalkanediyl" refers to a cyclic saturated divalent hydrocarbon radical having the number of carbon atoms indicated.

The terms "cycloalkenediyl" and "cycloalkynediyl" refer to cyclic unsaturated divalent hydrocarbon radicals. A "cycloalkenediyl" is characterized by a carbon-carbon double bond and a "cycloalkynediyl" is characterized by a carbon-carbon triple bond.

The term "arylenediyl" refers to a divalent unsaturated aromatic carbocyclic radical having one or two rings. The term "alkarylenediyl" refers to an arylenediyl substituted with one or more alkyl groups and the term "aralkylenediyl" refers to an alkylenediyl" substituted with one or more aryl groups.

The term "peptide bond" is used in its common accepted meaning.

The term "hydrolytically-labile bond" refers to a bond that is capable of undergoing hydrolysis, such as an ester, amide, acetal, or hydrazone bond. Preferably, the hydrolytically-labile bond is labile under acid conditions.

The term "halo" refers to chloro, bromo, iodo and fluoro atoms.

The term "saccharide" is used in its common accepted meaning. The terms "polysaccharide" and "oligosaccharide" refer to carbohydrate molecules containing more than one saccharide unit.

The term "activating/protecting group" refers to a group in a multifinctional compound which may temporarily activate or temporarily block a reactive site wherein a chemical reaction is to be carried out selectively at a reactive site. The reactive site may be other than the site occupied by the "activating/protecting group." The activating/protecting groups referred to, in the context of the present invention, are those commonly known activating/protecting groups including, but not limited to, activating groups such as N-succinimidyl, pentachlorophenyl, pentafluorophenyl, para-nitrophenyl, dinitrophenyl, N-phthalimido, N-norbornyl, cyanomethyl, pyridyl, trichlorotriazine, 5-chloroquinilino, and protecting groups such as N-(9-fluorenyl-methoxycarbonyl) (Fmoc), carbobenzyloxy (Cbz), 1-(4,4-dimethyl-2,6-dioxocyclohexylidene)-ethyl (Dde) and imidazolyl.

The term "prepolymer" refers to a reactant used to make a polymer, that is, to monomers and other subunits from which polymers may be formed.

The term "therapeutically effective amount" refers to the amount which, when administered to a patient for treating a disease, is sufficient to effect such treatment for the disease.

The term "treating" or "treatment" is intended to include inhibiting the disease (i.e., arresting its development) and relieving the disease (i.e., causing regression of the disease).

II. The Degradable Polymers

The novel degradable polymers are represented by Formula (I)

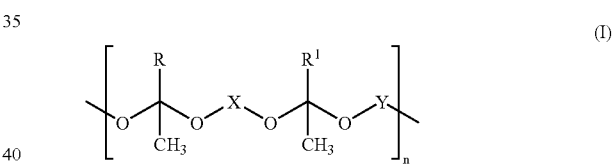

wherein R and $R^1$ are selected from the group consisting of hydrogen, $C_{1-18}$ alkyl, $C_{2-18}$ alkenyl, $C_{2-18}$ alkynyl, $C_{6-18}$ aryl, $C_{7-18}$ alkaryl and $C_{7-18}$ aralkyl groups;

X is a group capable of being covalently conjugated to a bioactive agent via a peptidic or a hydrolytically-labile bond;

Y is a group selected from the group consisting of $C_{1-200}$ alkanediyl, $C_{2-200}$ alkenediyl, $C_{2-200}$ alkynediyl, $C_{6-200}$ cycloalkanediyl, $C_{6-200}$ cycloalkenediyl, $C_{6-200}$ cycloalkynediyl, $C_{6-200}$ arylenediyl, $C_{6-200}$ alkarylenediyl, $C_{6-200}$ aralkylenediyl groups, or any of the above groups wherein the carbon backbone is substituted with one or more oxygen atoms within the carbon backbone; and n is an integer of 2–10,000.

III. Presently Preferred Embodiments

In a preferred embodiment, R and $R^1$ in Formula (I) are the same and are selected from hydrogen, $C_{1-12}$ alkyl, $C_{2-12}$ alkenyl, $C_{2-12}$ alkynyl, $C_{6-12}$ aryl, $C_{7-12}$ alkaryl and $C_{7-12}$ aralkyl groups; more preferably hydrogen, $C_{1-4}$ alkyl, $C_{2-4}$ alkenyl, $C_{2-4}$ alkynyl, $C_{6-10}$ aryl, $C_{7-10}$ alkaryl and $C_{7-10}$ aralkyl groups; most preferably hydrogen, $C_{1-4}$ alkyl, and $C_{2-4}$ alkenyl.

In a preferred embodiment X is a $C_{1-24}$ alkanediyl group, where the alkanediyl group is optionally substituted within the carbon backbone with one or more groups selected from C(O), C(O)NR$^1$, C(O)O, >NR$^{2'}$, wherein N is bound to two carbon atoms within the carbon backbone and R$^{2'}$ is hydrogen, or is a group capable of displacement so that N is capable of linking to a bioactive agent, or is a group capable of linking to a bioactive agent, —O— and —S—, and the alkanediyl group may comprise a pendant group or groups selected from haloaryl, haloalkyl, aryl, alkaryl, aralkyl, alkoxyaryl, alkoxyalkyl, aminoalkyl, mono-, di- and trialkylaminoalkyl, arylaminoalkyl, aminoacyl, N-aryl-N-alkylaminoalkyl aminoaryl, alkoxy, alkenyloxy, alkynyloxy, cycloalkoxy, cycloalkenyloxy, cycloalkynyloxy, haloalkoxy, aralkoxy, alkoxyaryloxy, alkoxyalkoxy, aminoalkoxy, mono-, di- and trialkylaminoalkoxy, arylaminoalkoxy, N-aryl-N-alkylamino-alkoxy, acyloxy, acyloxyalkyl, acylaminoalkyl, N-diacyl-iminoalkyl groups, acylamino, alkylamino and hydroxy groups.

In an embodiment of the invention, the alkanediyl group or the pendant group or groups comprises a primary, secondary, or tertiary amine group.

Most preferably, X does not comprise a saccharide, oligosaccharide or polysaccharide.

In the definition of X, any alkyl group or moiety is preferably $C_{1-18}$ alkyl, any alkenyl group or moiety is preferably $C_{2-18}$ alkenyl, any alkynyl group or moiety is preferably $C_{2-12}$ alkynyl, any aryl group or moiety is preferably $C_{6-24}$ aryl, any alkaryl group or moiety is preferably $C_{7-24}$ alkaryl and any aralkyl group or moiety is preferably $C_{7-24}$ aralkyl, any cycloalkyl group or moiety is preferably $C_{4-24}$ cycloalkyl, any cycloalkenyl group or moiety is preferably $C_{5-24}$ cycloalkenyl, and any cycloalkynyl group or moiety is preferably $C_{5-24}$ cycloalkynyl.

Most preferably X is selected from the groups (IV)–(VIII) below:

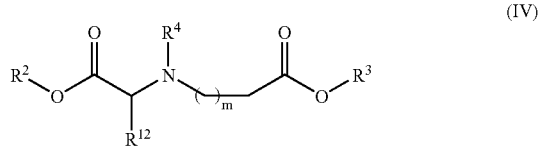
(IV)

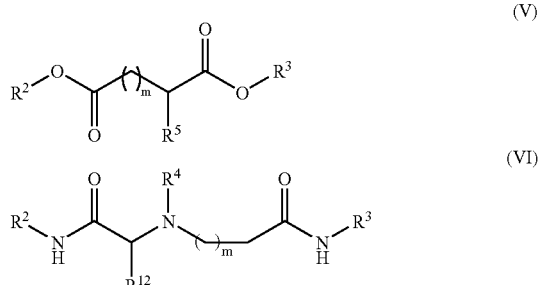
(V)

(VI)

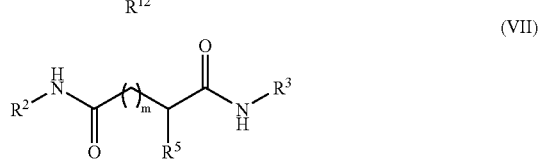
(VII)

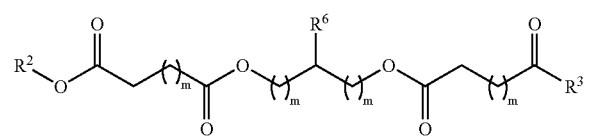
(VIII)

wherein R$^2$ and R$^3$ are independently selected from covalent bonds or $C_{1-18}$ alkanediyl groups terminating in OH or vinyl ether;

each R$^{12}$ is independently selected from synthetic or natural amino acid side chains;

each R$^4$ is independently selected from the group consisting of hydrogen, activating/protecting groups and the groups (IX), (X), (XI) and (XII)

(IX)

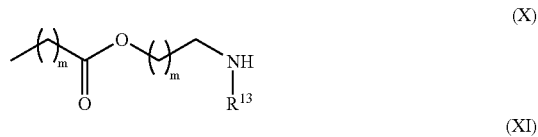
(X)

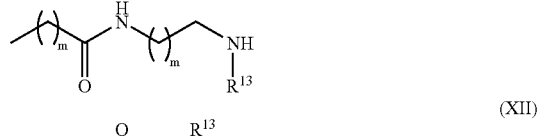
(XI)

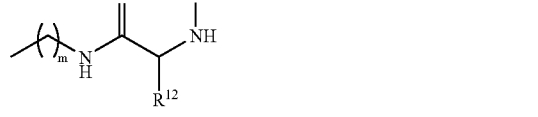
(XII)

R$^5$ and R$^6$ are selected from the group consisting of —NH$_2$, —NHR$^{13}$, —OR$^{13}$, wherein each R$^{13}$ is independently selected from hydrogen, $C_{1-4}$ alkyl, and activating/protecting groups; and m is an integer of 0–20.

Y preferably is represented by the formula —(C$_n$H$_{2n}$O)$_q$C$_n$H$_{2n}$—, wherein n is an integer of 2–10, preferably 2 or 3 and q is an integer of 1 to 200.

The molecular weight of the polymer of Formula (I) is preferably in the range of 10,000–100,000.

IV. Preparation of the Polymer of Formula (I)

The polymer of Formula I

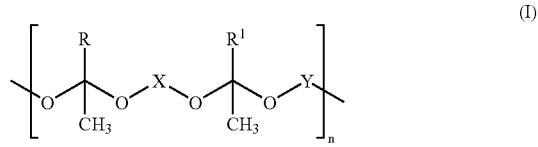
(I)

wherein R and R$^1$ are selected from the group consisting of hydrogen, $C_{1-18}$ alkyl, $C_{2-18}$ alkenyl, $C_{2-18}$ alkynyl, $C_{6-18}$ aryl, $C_{7-18}$ alkaryl and $C_{7-18}$ aralkyl groups;

X is a group capable of being covalently conjugated to a bioactive agent via a peptidic or a hydrolytically-labile bond;

Y is a group selected from the group consisting of $C_{1-200}$ alkanediyl, $C_{2-200}$ alkenediyl, $C_{2-200}$ alkynediyl, $C_{6-200}$ cycloalkanediyl, $C_{6-200}$ cycloalkenediyl, $C_{6-200}$ cycloalkynediyl, $C_{6-200}$ arylenediyl, $C_{6-200}$ alkarylenediyl, $C_{6-200}$ aralkylenediyl groups, or any of the above groups wherein the carbon backbone is substituted with one or more oxygen atoms within the carbon backbone; and n is an integer of 2–10,000 may be prepared by the reaction of a diol of Formula (II)

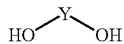
(II)

with a divinyl ether of Formula (III)

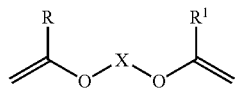
(III)

wherein R, R$^1$, X and Y are as defined above.

The diol of Formula (II) preferably is a polyethylene glycol or polypropylene glycol compound having a molecular weight in the range 100–20,000, more preferably polyethylene glycol having a molecular weight in the range 200–10,000, most preferably polyethylene glycol having a molecular weight in the range 200–5,000, in particular a molecular weight of approximately 200–4,000. Such materials are widely available from such commercial sources as Sigma-Aldrich Corporation (St. Louis, Mo.) and Shearwater Polymers. Inc. (Huntsville, Ala.). It will be understood by one of ordinary skill in the art that the reactant of Formula (II) may also comprise any diol of Formula (II), such as other glycols and diols suitable for use in biomaterials.

The divinyl ether of Formula (III) may be obtained commercially or may be made by any suitable means known in the art. For example, commercially-obtained amino vinyl ether may be combined with methyl esters to provide the divinyl ethers of Formula (III). Similarly, the hydroxy vinyl ether compound is commercially available, and may be used to make polyacetal polymers with ester moieties in the main chain. The methyl esters may comprise, for example, esters such as malonates, imines such as iminodiacetates, and other compounds known in the art. Symmetric, achiral methyl esters are preferred synthetic precursors.

The polymerization reaction may be carried out in a solventless system, although preferably the reaction takes place in the presence of an organic solvent selected from aliphatic or aromatic hydrocarbons, which may be optionally halogenated, ethers (including cyclic ethers), dialkylsulfoxides and alcohols (preferably sterically hindered alcohols, for example secondary or tertiary alcohols). Preferred solvents include tetrahydrofuran (THF), dichloromethane, and toluene. A particularly preferred solvent is toluene.

The polymerization is generally carried out in the presence of a suitable catalyst such as a catalyst for acid-catalysis, for example, hydrochloric acid, sulfuiric acid, phosphoric acid, p-toluenesulfonic acid, methanesulfonic acid, acetic acid, n-butyric acid, trifluoroacetic acid or oxalic acid. A preferred catalyst is p-toluene sulfonic acid (p-TSA).

The polymerization is conducted at a temperature of –10° C.–200° C., preferably 20° C.–120° C., most preferably between about 25° C. and 60° C.

V. Polyacetal Conjugates of Bioactive Agents and Their Preparation

The functionalized polymers of the invention comprise polymers with bioactive functionality, and thus comprise polymers that include bioactive agents. The degradable polyacetal polymers of the invention comprising bioactive functionality may be formed from substrates that include bioactive agents, from polymers to which bioactive agents are conjugated, and from substrates that combine to form bioactive agents.

A bioactive agent may be attached to X in Formula (I). In a particularly preferred embodiment, when X is (IX), (X), (XI), (XII), or >NR$^{2'}$, wherein N is bound to two carbon atoms within the carbon backbone and R$^{2'}$ is hydrogen, or is a group capable of displacement so that N is capable of linking to a bioactive agent, or is a group capable of linking to a bioactive agent, the N atoms of the groups >NR$^{2'}$, (IX), (X), (XI) and (XII) are, or are capable of being covalently attached to the bioactive agent.

The bioactive agent preferably is a pharmaceutically active agent (a "drug"). Suitable drugs include any drugs for which prolonged action and/or a targeted intracellular delivery is desirable, and include anticancer agents, for example doxorubicin, daunomycin, paclitaxel, taxotere, and the like, most preferably, doxorubicin. Other bioactive agents include polypeptides and proteins. The method of attachment may vary somewhat according to the bioactive agent, as is described below; and a person of ordinary skill in the art will be able, having selected a desired bioactive agent, using their knowledge and the disclosure of this application, to attach the bioactive agent to a degradable polyacetal polymer of this invention, thereby forming a conjugated polymer of this invention.

The attachment of the bioactive agent to the polymer of Formula (I) may be effected by the reaction of the polymer with the bioactive agent or a bioactive agent precursor. Bioactive agents may be attached to the polymer in any suitable manner. Preferably the attachment is effected subsequent to the polymerization reaction to produce the degradable polymer of Formula (I).

Attachment of bioactive agents may be effected in other ways as well. For example, attachment may be by linkages comprised of groups that covalently couple and cross-link the agents to the polymers. Such linkages may comprise disulfide linkages or ester bonds, or may be acid-labile linkages such as hydrazone linkage as described by Greenfield et al., Cancer Res., 50, 6600–6607 (1990), and references therein. Alternatively, the attachment may be via a "protected" disulfide bond that sterically inhibits attack from thiolate ions, such as are found in the coupling agents S-4-succinimidyloxycarbonyl-α-methyl benzyl thiosulfate (SMBT) and 4-succinimidyloxycarbonyl-.alpha.-methyl-α-(2-pyridyldithio) toluene (SMPT), in the manner disclosed in U.S. Pat. No. 6,048,736 to Kosak.

Where the bioactive agent has an amino group, it may be useful to form a reactive carbonate half ester in the polymer, P, P-O—CO—X, wherein X is a good leaving group, using reagents such as carbonyl diimidazole, p-nitrophenyl chloroformate or bis-N-succinimidyl carbonate. The activated polymer P, P-O—CO—X, may then be reacted with the bioactive agent under conditions which do not destroy its activity, leading predominantly to urethane linkages attached through the amino group. For example, carbonyl diimidazole, can be reacted with terminal hydroxyl groups of the polymer. The reaction mixture may be quenched in aqueous solution at neutral pH and the activated polymer isolated, for example by dialysis or size exclusion chromatography, as disclosed in U.S. Pat. No. 5,468,478 to Saifer et al.

Attachment (conjugation) of bioactive agents may be effected by reaction with polymers or monomers with electrophilic functionality. For example, prepolymers comprising electrophilic pendant chain functionalized monomers which comprise, for example, diols or bis-vinyl ethers, may be used for this purpose.

The following reaction scheme illustrates one route to the production of a polymer-doxorubicin drug conjugate:

Scheme 2

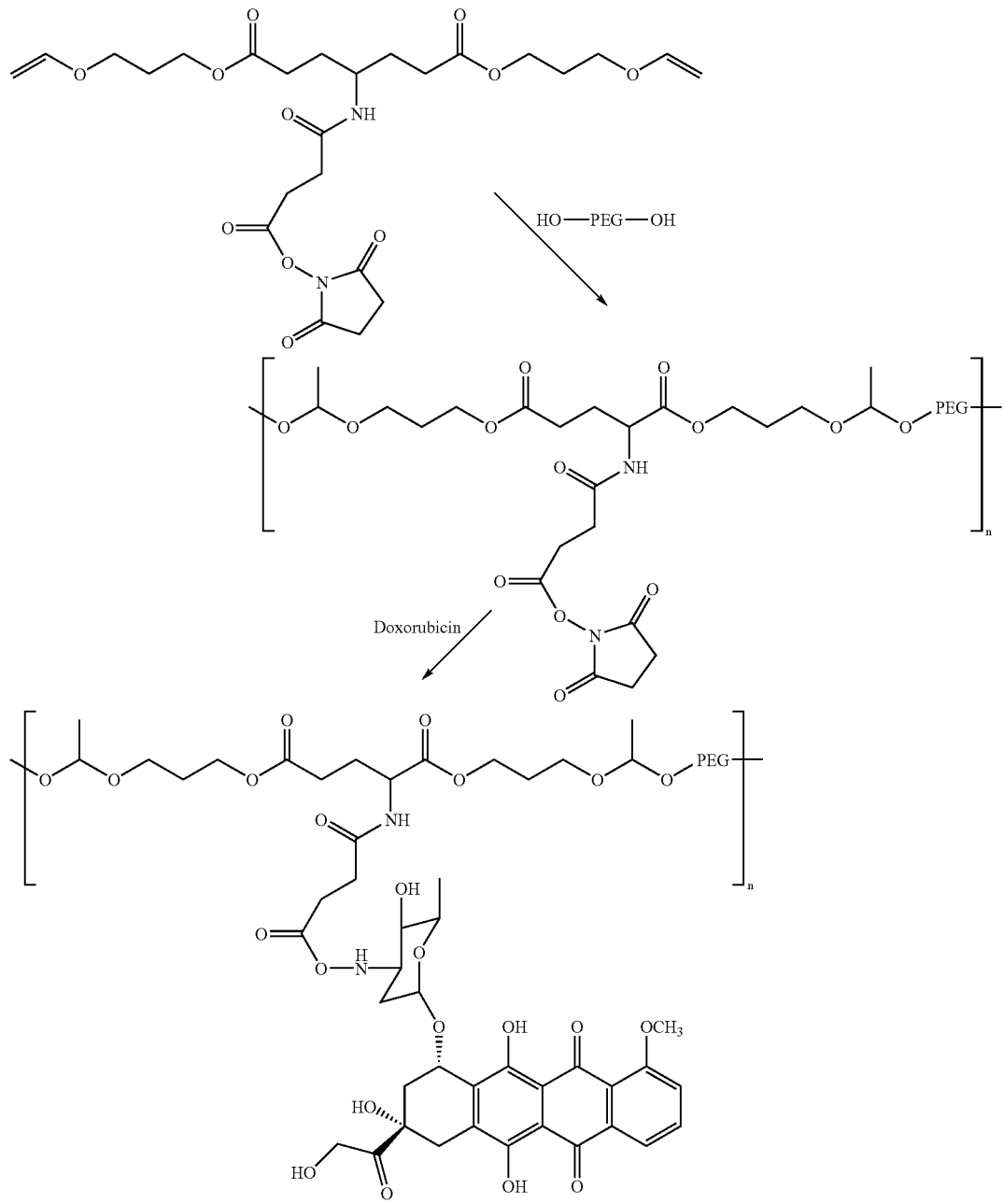

In this scheme, PEG is the residue of a polyethylene glycol (without the terminal hydroxy groups), the termninal OH groups of the polyethylene glycol being explicitly shown when the entire glycol is meant.

Bioactive agents that may be attached (conjugated) to the polyacetal polymers of the invention include polypeptides and proteins. Such conjugation may be effected at pendant chains and at termninal groups. For example, conjugated polyacetal polymers of the invention include proteins conjugated with a degradable polyacetal polymer.

VI. Administration and Pharmaceutical Composition

Compositions comprising the degradable polyacetal polymers, with or without attached bioactive agents, are water-soluble or colloidal suspension compositions suitable for incorporation into pharmaceutical solutions or pharmaceutical compositions, or for delivery to an animal or patient for treatment. For example, polyacetal polymers of the invention are soluble in water and water solutions, such as saline, phosphate buffered saline (PBS), and other buffered solutions. The polyacetal polymers are soluble in solutions of widely varying pH.

In general, degradable polyacetal polymer compositions will be administered in therapeutically effective amounts by any of the usual modes known in the art. Degradable polyacetal polymers with attached bioactive agents may be directly delivered to solutions bathing cells, tissues or organs in vitro. Pharmaceutical compositions comprising bioactive agents attached to degradable polyacetal polymers may be administered to an animal, including a human, by one of the following routes: oral, topical, systemic (e.g. transdermal, intranasal, or by suppository), or parenteral (e.g. intramuscular, subcutaneous, or intravenous injection). Compositions may take the form of tablets, pills, capsules, semisolids, powders, sustained release formulations, solutions, suspensions, elixirs, aerosols, or any other appropriate compositions; and comprise a bioactive agent attached to a degradable polyacetal polymer of the invention in combination with at least one pharmaceutically acceptable excipient. Suitable excipients are well known to persons of ordinary skill in the art, and they, and the methods of formulating the compositions, may be found in such standard references as Alfonso AR: *Remington's Pharmaceutical Sciences*, 17th ed., Mack Publishing Company, Easton Pa., 1985. Suitable liquid carriers, especially for injectable solutions, include water, aqueous saline solution, aqueous dextrose solution, and glycols.

Pharmaceutical formulations comprising bioactive agents attached to degradable polyacetal polymers of the invention can be prepared according to any method known to the art for the manufacture of pharmaceuticals. Such formulations can contain sweetening agents, flavoring agents, coloring agents and preserving agents. Any such formulation can be admixed with nontoxic pharmaceutically acceptable excipients which are suitable for manufacture.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient.

Intravenous injectable compositions are comprised of a polymer-drug conjugate of the invention in combination with at least one pharmaceutically acceptable liquid carrier. Acceptable liquid carriers are non-toxic, aid administration, and do not adversely affect the therapeutic benefit of the polymer-drug conjugate. Such suitable carriers include, but are not limited to, water, saline, aqueous dextrose and glycols. Further, excipients and other agents may be included in pharmaceutical compositions along with the degradable polyacetal polymers and attached bioactive agents. In addition, other additives and agents, such as antioxidants, antiseptic or antibiotic agents, buffers, stabilizers, solubilizers and other agents, may be added to degradable polyacetal polymer compositions of the invention. For example, dimethylsulfoxide, benzoic acid, ascorbic acid, or tocopherol may be included in pharmaceutical compositions comprising degradable polyacetal polymer compositions of the invention. Thus, injectable compositions comprising bioactive agents conjugated to degradable polyacetal polymers will preferably comprise water or saline solutions or emulsions, pharmaceutically acceptable carriers, and may further comprise buffering agents, such as phosphate buffer or HEPES buffer, and optionally other agents.

In general, the polymer-drug conjugates of the invention will be administered in therapeutically effective amounts via intravenous injection. A therapeutically effective amount may vary depending on the severity of the disease, the age and relative health of the subject, the potency of the conjugate used and other factors. A therapeutically effective amount may range from about 0.001 milligram per Kg (mg/Kg) body weight per day to 100 mg/Kg body weight per day. Preferably the amount will be about 0.1 to 10 mg/Kg/day. Therefore, a therapeutically effective amount for a 70 Kg patient may range from about 0.07 to 7000 mg/day, preferably about 7 to 700 mg/day. A person of ordinary skill in the art of treating diseases such as cancer will, without undue experimentation, having regard to that skill and this disclosure, be able to determine a therapeutically effective amount of a particular bioactive agent attached to a degradable polyacetal polymer for practice of this invention.

The degradable polyacetal polymers of the invention, with or without attached bioactive agents, may be dried or lyophilized and stored in that condition for a considerable length of time without significant degradation or decomposition. Such dried or lyophilized compositions may be reconstituted for use, e.g., for injection, at a convenient time after storage by addition of an appropriate amount of a suitable liquid, preferably a buffered water solution, such as saline. An appropriate amount is that amount sufficient to provide the desired volume so as to result in a solution of the desired final concentration.

Excipients useful for preparation of lyophilized or freeze-dried compositions include saccharides, amino acids, and salts such as inorganic salts. Saccharides may be, for example, monosaccharides, such as glucose and fructose, disaccharides such as maltose, lactose, and sucrose, polysaccharides such as dextran and starch, and sugar alcohols, such as mannitol sorbitol and glycerol. Amino acids may include, for example, glycine, and salts may include, for example, sodium chloride and potassium chloride. Such excipients may be used alone or in combination, and may be useful for inhibiting aggregation in the reconstituted polymer solution.

The amount of a polymer-drug conjugate of the invention in the composition may vary. In general, the final composition will comprise from about 0.001% w/w to 30% w/w of the polymer-drug conjugate, preferably about 0.01% w/w to 10% w/w, more preferably about 0.1% w/w to 5% w/w with the remainder being the carrier or carriers.

VII. Pharmacology and Utility

Degradable polymers are useful in a wide variety of pharmaceutical and biomedical applications. Uses for degradable polymers include coatings for drug tablets, contact lens coatings, coatings for surgical implants and medical devices, gels, as ingredients in topical and optical pharmaceutical solutions, in pharmaceutical formulations including delayed release pharmaceutical formulations and in targeted drug formulations. Conjugation of bioactive agents, such as anticancer drugs, with degradable polymers helps to enhance the efficacy of the bioactive agent.

Degradable polyacetal polymers of the invention are suitable for use in pharmaceutical and biomedical applications with superior properties compared to prior materials. The polyacetal polymers of the invention are degradable under physiological conditions on a time-scale suitable for effective delivery of bioactive agents in an animal. In addition, the biodistribution of degradable polyacetal polymers of the invention within the body and bloodstream of the animal receiving the polymer is favorable for the effective delivery of bioactive agents for the treatment of many diseases. The polymers and bioactive agents remain in the bloodstream for hours, not minutes, do not preferentially go to the liver, but remain in circulation so as to provide for the prolonged action of the bioactive agents, and are not toxic.

Figure 2:
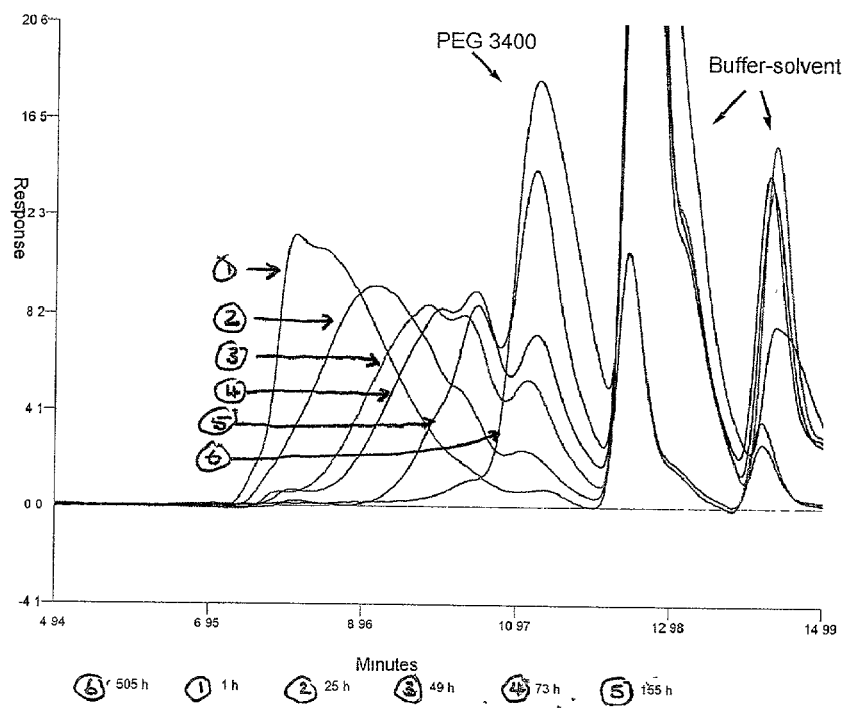
FIG. 2 is a graph showing the superposition of gel permeation chromatography traces for polyacetal 3 dissolved in solution at pH 5.5 and at 37° C. over a period of 21 days.
Figure 3:
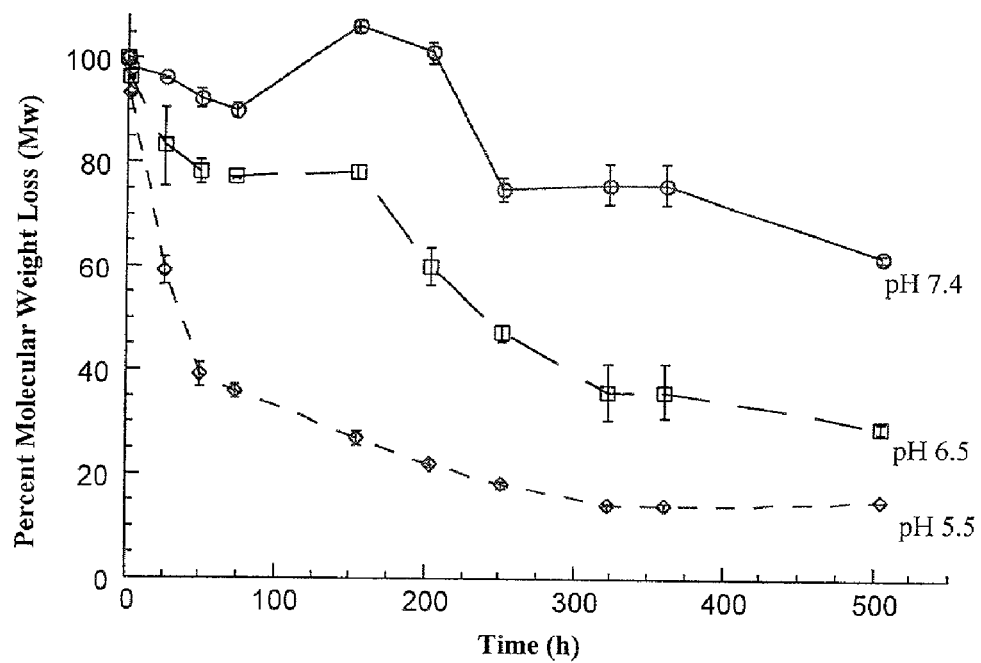
FIG. 3 is a graph showing polyacetal 3 degradation shown as percent molecular weight loss at pH values of 7.4, 6.5 and 5.5 versus time.

The stability of the degradable polyacetals of the invention differs in solutions of different pH. Degradable polyacetals of the invention are quite stable in water solutions near neutral pH, less so in more acidic solutions. As shown in FIG. 1, polyacetal 3 (at pH 7 and at 37° C.) was quite stable, with little change in the molecular weight at time points ranging from 1 to 505 h (21 days). However, polyacetal 3 was less stable when dissolved at pH 5.5 at 37° C. As shown in FIG. 2, polyacetal 3 had essentially degraded to the PEG monomeric units by 155 h (6.5 days). The results of three such stability experiments are shown in FIG. 3, in which the degradation of polyacetal 3 over time is shown as the percent molecular weight loss (Mw) at each pH value vs. time for the pH 5.5, 6.5 and 7.4.

Figure 4:
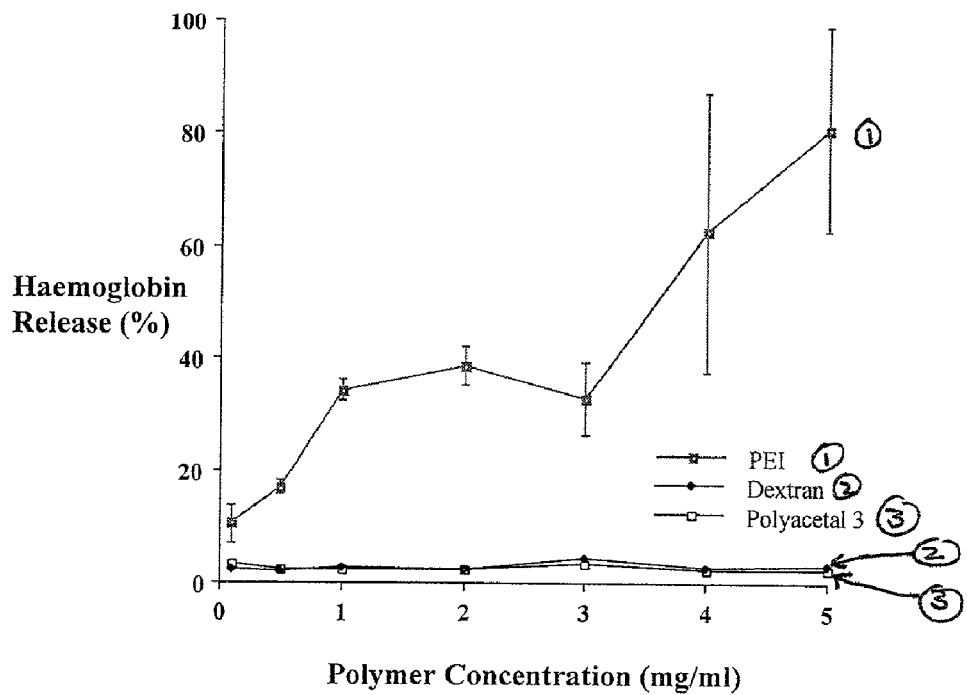
FIG. 4 is a graph showing red blood cell lysis assay of polyacetal 3.
Figure 5:
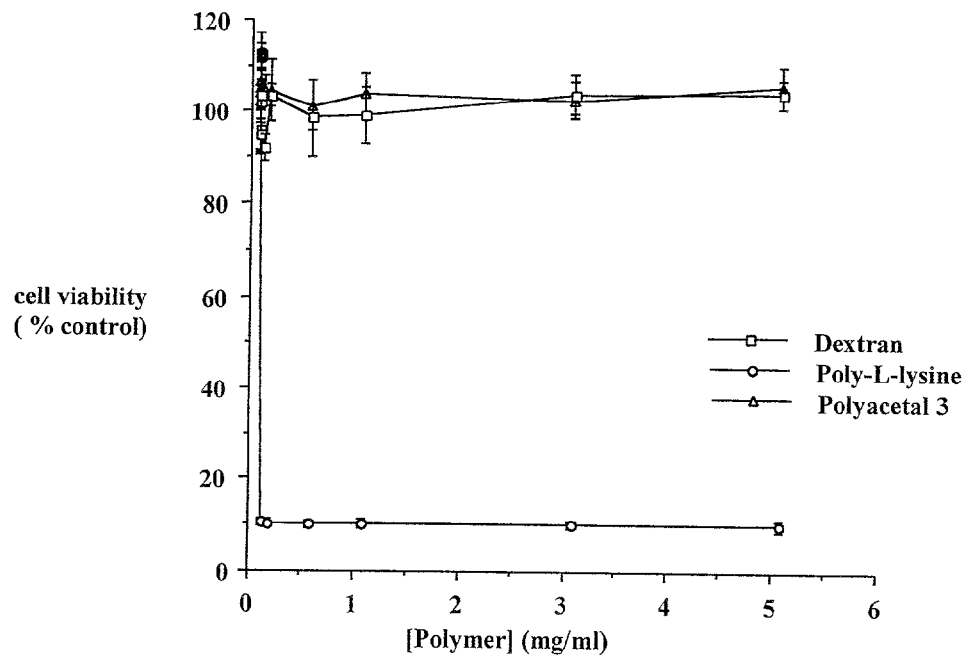
FIG. 5 is a graph showing the cytotoxicity of polyacetal 3 using the B16F10 cell line.

The polyacetal polymers of the invention are not toxic to cells. This is shown in FIG. 4, which present the results of a red blood cell (RBC) lysis assay of amino polyacetal 3. No RBC lysis was observed in this assay for polyacetal 3. Dextran was the control which did not display RBC lysis, while poly(ethylene imine) (PEI) was the control which caused RBC lysis. In addition, direct measurements of cell toxicity on cells in culture resulted in no measured cytotoxicity. As shown in FIG. 5, the cytotoxicity of polyacetal 3 was measured using the B16F10 cell line. Polyacetal 3 did not display cytotoxicity in this assay compared to polylysine which was used as a cytotoxic control. Dextran was used as a noncytotoxic control.

Figure 6:
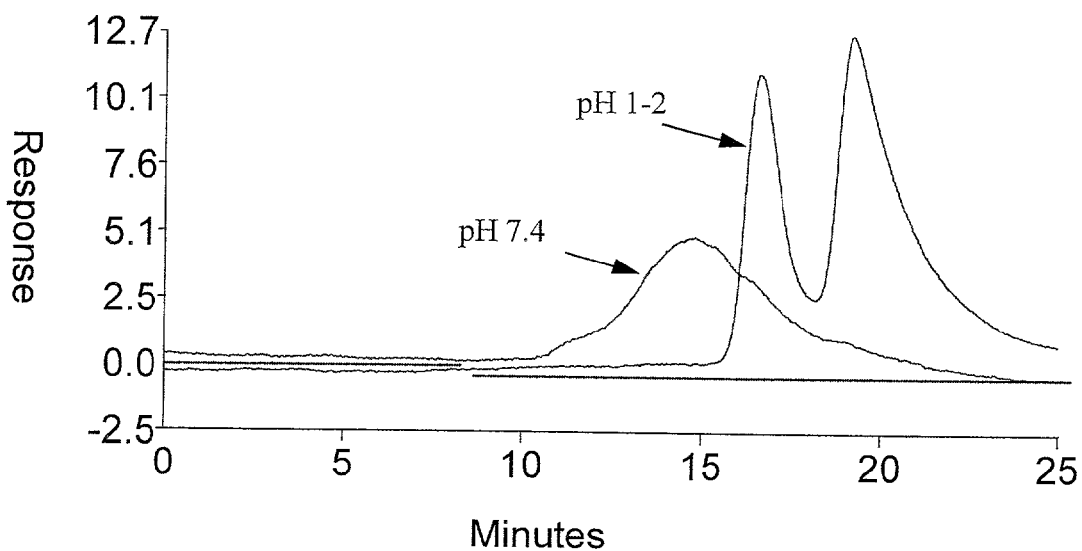
FIG. 6 is a graph showing superimposed gel permeation chromatography (GPC) traces of polyacetal 22 from a phosphate buffer solution at pH 7.4 and a solution where the pH was adjusted to 1–2 by the addition of HCl.
Figure 7:
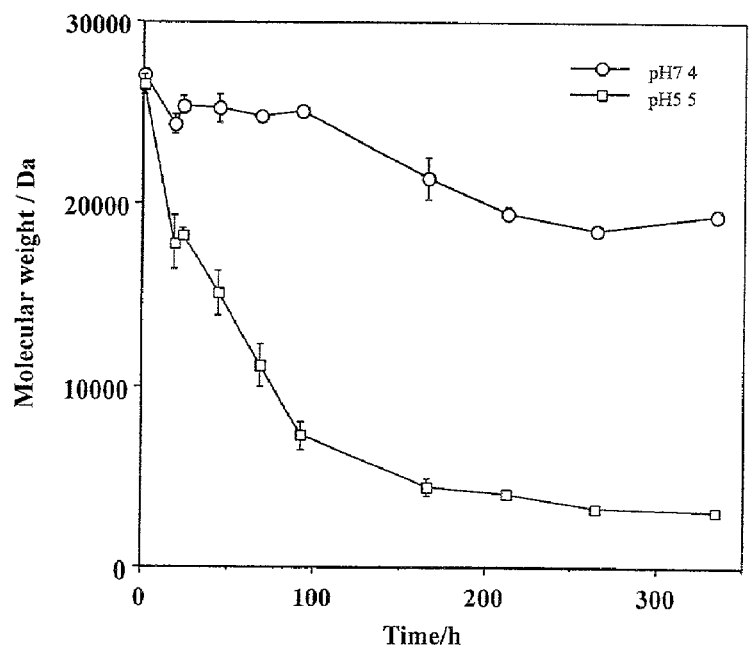
FIG. 7 is a graph showing the degradation profile of polyacetal 22 at pH 7.4 and 5.5 displaying the loss in molecular weight (Mw).

Similar to the results shown with polyacetal polymer 3, polyacetal polymer 22 is also sensitive to pH. This is shown in FIG. 6, in which are shown superimposed GPC traces of amino polyacetal 22 from a phosphate buffered solution at pH 7.4 and a solution where the pH was adjusted to pH 1–2 by addition of HCl. The polyacetal 22 completely degraded within minutes upon exposure at pH 1–2 to give the trace shown by the arrow labeled pH 1–2. This GPC trace is consistent with the molecular weight of $PEG_{3,400}$. The degradation profile of amino polyacetal 22 at pH 7.5 and pH 5.5 is shown in FIG. 7, where the loss in molecular weight is shown as a function of time. The degradation study shown in FIG. 7 was conducted at 37° C. and at a concentration of 3 mg/ml of polyacetal 22; three separate samples were analyzed at each pH. Polyacetal 22 degrades more rapidly in the mildly acidic medium at pH 5.5 than in the relatively neutral physiological pH 7.4. Lysosomal pH is in the range of pH 5.0 to pH 5.5. The experimental pH value of 5.5 was selected to match the lysosomal pH, which would be that encountered by a physiologically soluble polymer conjugate upon cellular uptake by endocytosis within the lysosome.

Figure 8A:
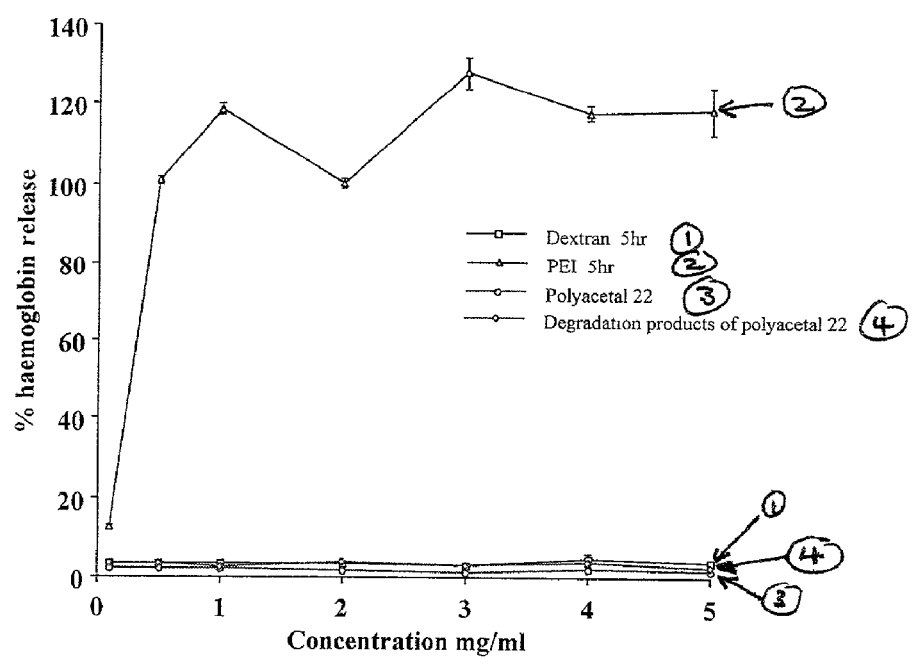
FIG. 8a is a graph showing red blood cell (RBC) lysis of polyacetal 22 and its degradation products over a 1 hour time period. No RBC lysis was observed in this assay for the polyacetal.
Figure 8B:
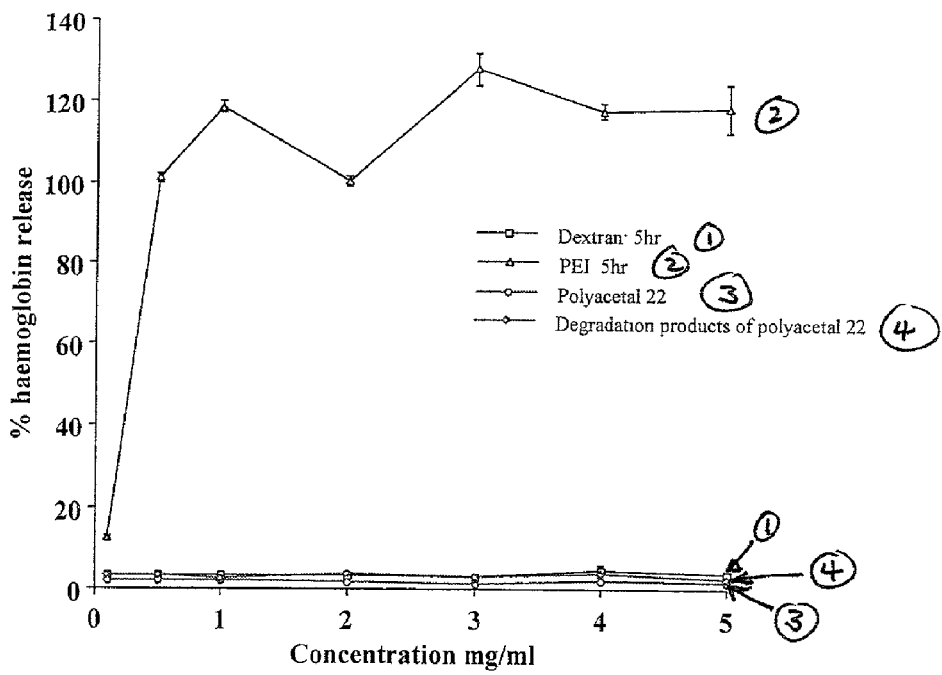
FIG. 8b is a graph showing red blood cell lysis of polyacetal 22 and its degradation products over a 5 hour time period. No RBC lysis was observed in this assay for the polyacetal.
Figure 9:
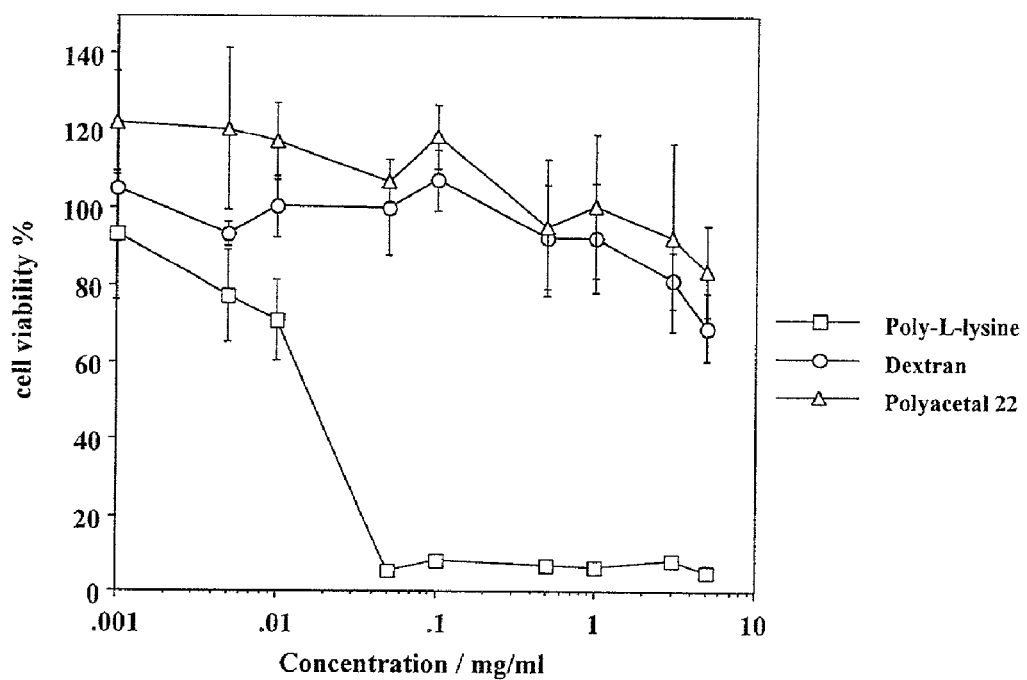
FIG. 9 is a graph showing cytotoxicity of polyacetal 22 using the B16F10 cell line. Polyacetal 22 does not display cytotoxicity in this assay.

The in vitro biocompatibility of amino polyacetal 22 is shown in FIGS. 8a, 8b, and 9. FIG. 8a shows the results of red blood cell lysis experiments at 1 hour, and FIG. 8b shows the results of red blood cell lysis experiments at 5 hours. FIG. 9 shows the results of cytotoxicity experiments. These experiments show that polyacetal 22 is not lytic or toxic to these cells, and so has a favorable biocompatibility profile.

Polyacetal polymers of the invention do not cause lysis of red blood cells. The results of a red blood cell (RBC) lysis assay of amino polyacetal 22 and its degradation products is shown over a 1 hour time period in FIG. 8a. The degradation products were obtained by dissolving polyacetal 22 in phosphate buffered saline (PBS), adjusting the pH to 1–2 by the addition of HCl to allow the polyacetal to degrade, then adding a small amount of NaOH to readjust the pH to 7.4. No RBC lysis was observed in this assay for polyacetal 22. Dextran was used as a control; it did not display RBC lysis. Poly(ethylene imine) (PEI) was also used as a control; it caused RBC lysis. Similarly, in FIG. 8b, the results of a red blood cell lysis assay of amino polyacetal 22 and its degradation products are shown over a 5 hour time period. No RBC lysis was observed in this assay for polyacetal 22. Dextran and poly(ethylene imine) (PEI) were used as control compounds again: dextran did not display RBC lysis, while PEI did cause RBC lysis. Thus, the results shown in FIGS. 8a and 8b demonstrate that the polyacetal polymer of the invention, polyacetal 22, was not lytic for red blood cells for up to five hours.

In addition, polyacetal polymers of the invention are not cytotoxic. A cytotoxicity assay of amine pendant chain polyacetal 22 using B16F10 cell line is shown in FIG. 9. As shown in FIG. 9, polylysine is cytotoxic at concentrations well below 0.1 mg/ml. However, polyacetal 22 did not display cytotoxicity in this assay at concentrations of up to several mg/ml, and thus is extremely well tolerated by these cells as compared to the cytotoxic control compound, polylysine. Dextran, used as a noncytotoxic control, was also found not to be cytotoxic even at relatively high concentrations.

Figure 10:
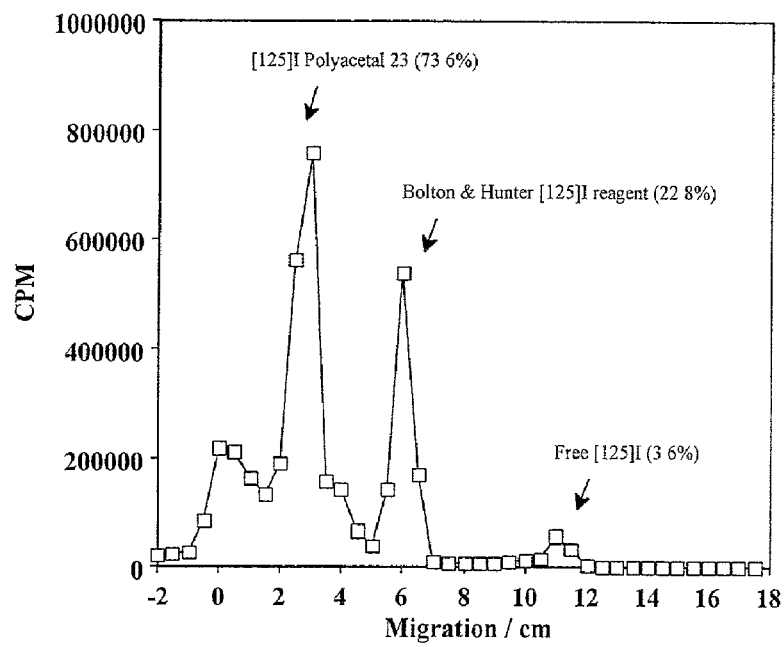
FIG. 10 is a graph showing the labeling efficiency with $^{125}$I labeled Bolton-Hunter reagent of polyacetal 22 to give conjugate polyacetal 23. This Figure shows the crude product.
Figure 11:
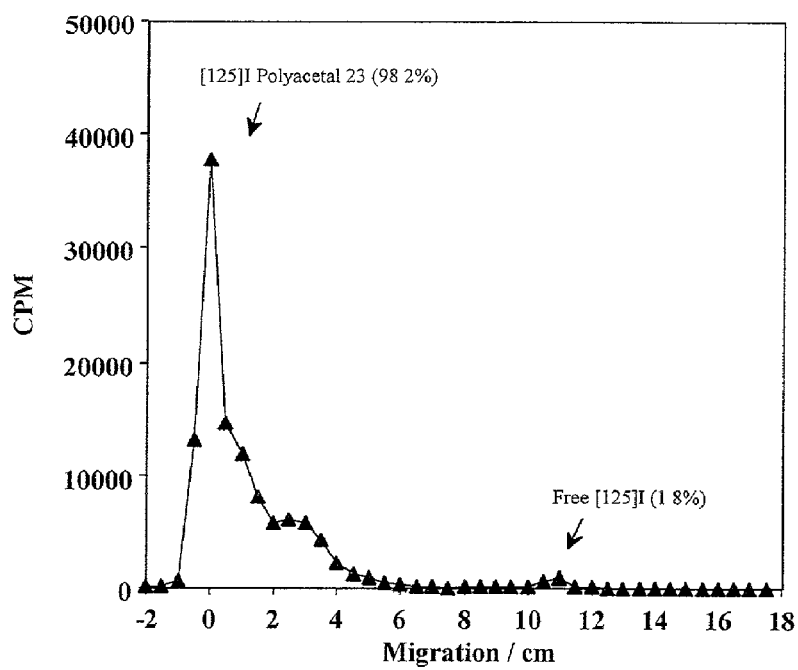
FIG. 11 is a graph showing the labeling efficiency with $^{125}$I labeled Bolton-Hunter reagent of polyacetal 22 to give conjugate polyacetal 23. This Figure shows the purified conjugate product.

Polyacetals of the invention remain in circulation in the blood with relatively little loss from the blood circulation to the organs. $^{125}I$ labeled polyacetal polymers of the invention may be formed using Bolton-Hunter methods, as shown in FIGS. 10 and 11 and described in Example 7. In the body distribution study shown in FIG. 12, polyacetal 23 was predominantly in the blood, at both at 5 min and at 1 hour after administration. The continued presence of polyacetal 23 in the blood in significant amounts at one hour is a surprising and favorable property of the polyacetal of the invention. This study shows that polyacetal 23 remains in the blood without accumulating in the organs shown. In particular, and in contrast to many previously-known polymers, the polyacetal of the invention is not significantly taken up by the liver but remains substantially in circulation in the blood for an hour. Thus, the polyacetal of the invention possesses the favorable properties of long-duration presence in the blood, of very little removal from circulation by the organs, and, since very little of the polyacetal is lost to the liver, relatively little degradation by the liver.

Figure 12:
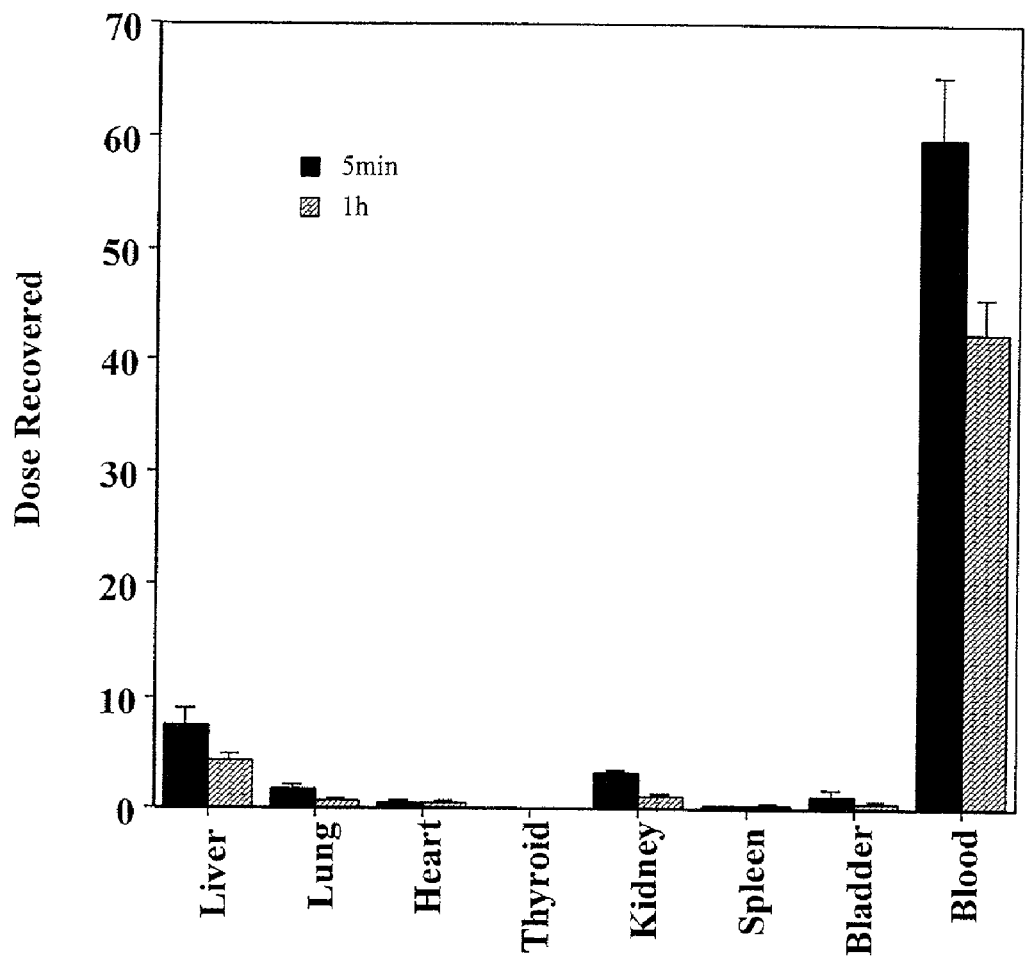
FIG. 12 is a graph showing the body distribution of radiolabeled polyacetal 23 conjugate at 5 min and 1 hour. This shows that the polyacetal conjugate remains in the blood without accumulating in the organs shown.

Functionalized polymers of the invention, such as may be formed by synthesis from functionalized precursors or by attachment of bioactive agents, such as anticancer drugs, to degradable polyacetal polymers of the invention may be effective to enhance the efficacy of the bioactive agent. As shown in FIG. 12, polyacetal polymers remain in circulation with relatively little removal or loss from the blood on a timescale of hours, a property which enhances the effectiveness of anticancer drugs attached to degradable polyacetal polymers of the invention. Higher dosages of the anticancer drugs, which are more effective in treating the cancerous tissue than lower dosages, are tolerated by animals when anticancer drugs are attached to degradable polyacetal polymers of the invention.

VIII. Prepolymers of Formula (XIII)

The prepolymers are novel divinylethers represented by Formula (XIII)

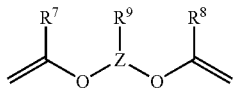
(XIII)

wherein $R^7$ and $R^8$ are selected from the same groups as R and $R^1$, Z is a $C_{1-24}$ alkanediyl group, optionally substituted within the carbon backbone with one or more or a mixture of the groups selected from carbonyl, peptide, ester, >$NR^{2'}$, wherein N is bound to two carbon atoms within the carbon backbone and $R^{2'}$ is hydrogen, or is a group capable of displacement so that N is capable of linking to a bioactive agent, or is a group capable of linking to a bioactive agent, —O— and —S—, and the alkanediyl group comprises a pendant group $R^9$, wherein $R^9$, is selected from haloaryl, haloalkyl, aryl, alkaryl, aralkyl, alkoxyaryl, alkoxyalkyl, aminoalkyl, mono-, di- and tri-alkylaminoalkyl, arylaminoalkyl, aminoacyl, N-aryl-N-alkylaminoalkyl aminoaryl, alkoxy, alkenyloxy, alkynyloxy, cycloalkoxy, cycloalkenyloxy, cycloalkynyloxy, haloalkoxy, aralkoxy, alkoxyaryloxy, alkoxyalkoxy, aminoalkoxy, mono-, di- and trialkylamninoalkoxy, arylaminoalkoxy, N-aryl-N-alkylamino-alkoxy, acyloxy, acyloxyalkyl, acylaminoalkyl, N-diacyl-iminoalkyl groups, acylamino, alkylamino and hydroxy groups.

In a preferred embodiment, $R^9$ contains at least one activating/protecting group.

In the definition of Z, any alkyl group or moiety is preferably $C_{1-18}$ alkyl, any alkenyl group or moiety is preferably $C_{2-18}$ alkenyl, any alkynyl group or moiety is preferably $C_{2-12}$ alkynyl, any aryl group or moiety is preferably $C_{6-24}$ aryl, any alkaryl group or moiety is preferably $C_{7-24}$ alkaryl and any aralkyl group or moiety is preferably $C_{7-24}$ aralkyl, any cycloalkyl group or moiety is preferably $C_{4-24}$ cycloalkyl, any cycloalkenyl group or moiety is preferably $C_{5-24}$ cycloalkenyl, and any cycloalkynyl group or moiety is preferably $C_{5-24}$ cycloalkynyl. Symmetric achiral methyl esters are preferred synthetic precursors.

Preferably Z has a structure (XIV), (XV), (XVI), (XVII) and (XVIII), below:

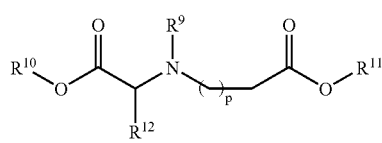
(XIV)

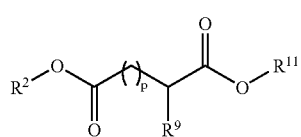
(XV)

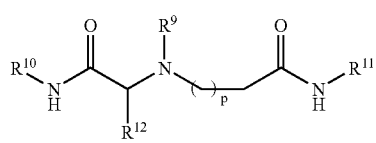
(XVI)

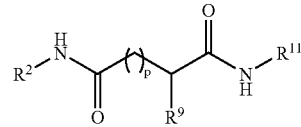
(XVII)

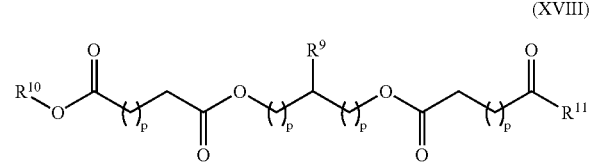
(XVIII)

wherein $R^{10}$ and $R^{11}$ are selected from covalent bonds, and $C_{1-6}$ alkanediyl groups;

$R^9$ is as defined above, $R^{12}$ are selected from synthetic or natural amino acid side chains; and p is an integer of 0–20.

Prepolymers as disclosed herein may be formed by any suitable method, including such methods as are disclosed in the Examples, such as Examples 3, 4 and following.

A process for the preparation of a prepolymer of Formula (XIII) may comprise the following steps. To prepare a prepolymer of Formula (XIII):

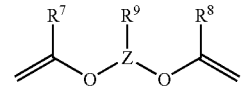
(XIII)

wherein $R^7$ and $R^8$ are selected from the group consisting of hydrogen, $C_{1-18}$ alkyl, $C_{2-18}$ alkenyl, $C_{2-18}$ alkynyl, $C_{6-18}$ a aryl, $C_{7-18}$ alkaryl and $C_{7-18}$ aralkyl groups;

Z is a $C_{1-24}$ alkanediyl group, where the alkanediyl group is optionally substituted within the carbon backbone with one or more groups selected from C(O), C(O)$NR^1$, C(O)O, >$NR^{2'}$, wherein N is bound to two carbon atoms within the carbon backbone and $R^{2'}$ is hydrogen, or is a group capable of displacement so that N is capable of linking to a bioactive agent, or is a group capable of linking to a bioactive agent, —O— and —S—, and the alkanediyl group comprises a pendant group $R^9$ selected from haloaryl, haloalkyl, aryl, alkaryl, aralkyl, alkoxyaryl, alkoxyalkyl, aminoalkyl, mono-, di- and tri-alkylaminoalkyl, arylaminoalkyl, aminoacyl, N-aryl-N-alkylaminoalkyl aminoaryl, alkoxy, alkenyloxy, alkynyloxy, cycloalkoxy, cycloalkenyloxy, cycloalkynyloxy, haloalkoxy, aralkoxy, alkoxyaryloxy, alkoxyalkoxy, aminoalkoxy, mono-, di- and trialkylaminoalkoxy, arylaminoalkoxy, N-aryl-N-alkylamino-alkoxy, acyloxy, acyloxyalkyl; acylaminoalkyl, N-diacyl-iminoalkyl groups, acylamino, alkylamino and hydroxy groups;

the steps of the process comprise:

reacting a methyl ester of Formula (XIX)

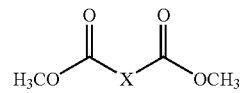
(XIX)

with a vinylether of Formula (XX)

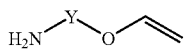

(XX)

or Formula (XXI)

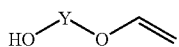

(XXI)

wherein X comprises a group capable of being covalently conjugated to a bioactive agent via a peptidic or a hydrolytically-labile bond, and Y is a group selected from the group consisting of linear and branched $C_{1-200}$ alkanediyl, $C_{2-200}$ alkenediyl, $C_{2-200}$ alkynediyl, $C_{6-200}$ cycloalkanediyl, $C_{6-200}$ cycloalkenediyl, $C_{6-200}$ cycloalkynediyl, $C_{6-200}$ arylenediyl, $C_{7-200}$ alkarylenediyl, $C_{7-200}$ aralkylenediyl groups, or any of the above groups wherein the carbon backbone is substituted with one or more oxygen atoms within the carbon backbone.

In a preferred embodiment of the method of preparing a prepolymer of Formula (XIII), $R^9$ contains at least one activating/protecting group.

These prepolymers are particularly useful for the preparation of the polymers of Formula (I) by methods known in the art and as illustrated in the Examples. Functionalized prepolymers, such as prepolymers functionalized with bioactive agents or precursors to bioactive agents, are useful for the preparation of polymers of formula comprising bioactive agents. The following structures represent some particularly preferred prepolymers of the present invention.

Scheme 1

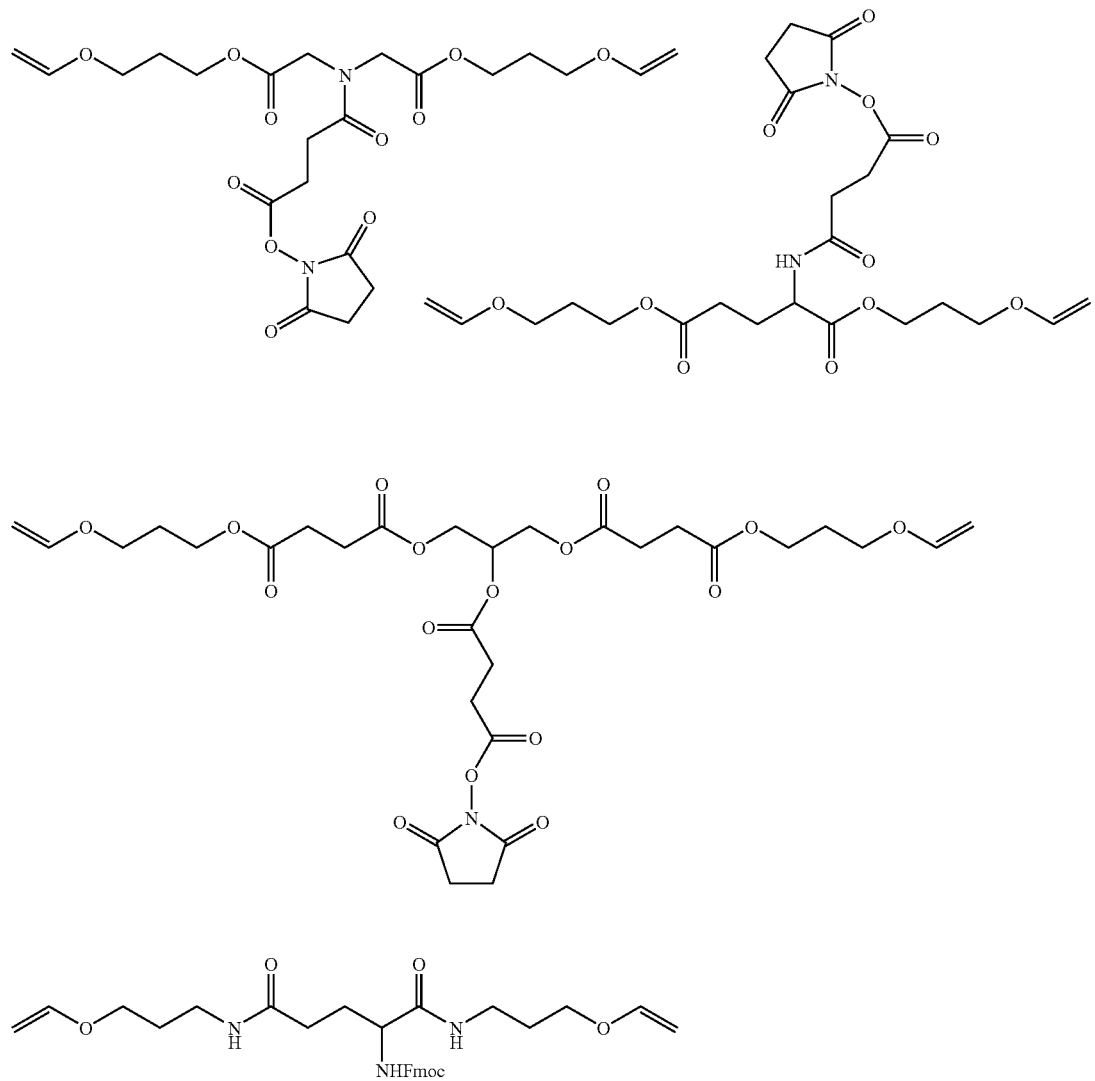

-continued

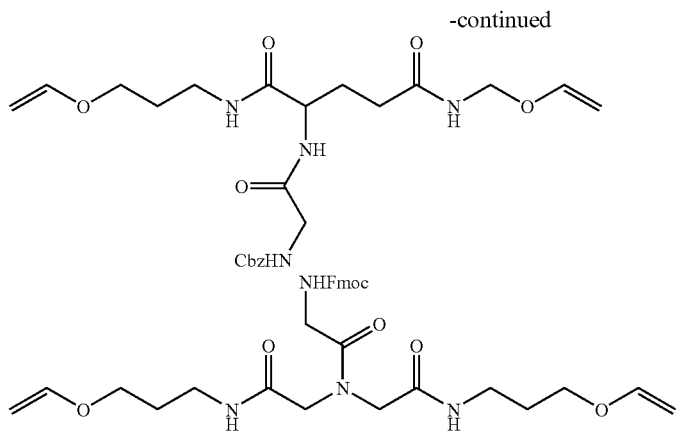

EXAMPLES

General

The degradable polymers of the present invention may be prepared by the reaction of poly(ethylene glycol) (PEG) as the source of diol (PEG's with molecular weights of 3,400 g/mol were used) and commercially available triethylene glycol di-vinyl ether. PEG is selected as the diol because it is generally recognized as safe (GRAS) by drug regulatory authorities and is widely used in pharmaceutical formulation. However, it will be appreciated by those of ordinary skill in the art that other diols, including PEGs of lower or higher molecular weight, are also suitable for the practice of the invention. The use of the unfunctionalized divinyl ether, triethylene glycol di-vinyl ether, in the preliminary experiments was conducted to confirm a suitable degradation profile (needed for lysosomal degradation) and to confirm in vitro biocompatibility. It will be understood by one of ordinary skill in the art that degradable polyacetal polymers of the invention may also be prepared from functionalized starting materials. For example, functionalized vinyl ethers, particularly functionalized divinyl ethers, may be used as starting materials in the preparation of the degradable polyacetal polymers of the invention. Each following experimental example is preceded by a scheme summarizing the reaction involved. In each case m is an integer representing a PEG molecule of the identified molecular weight Mn.

Example 1

Synthesis of Polyacetal 3 by Polymerization in Toluene

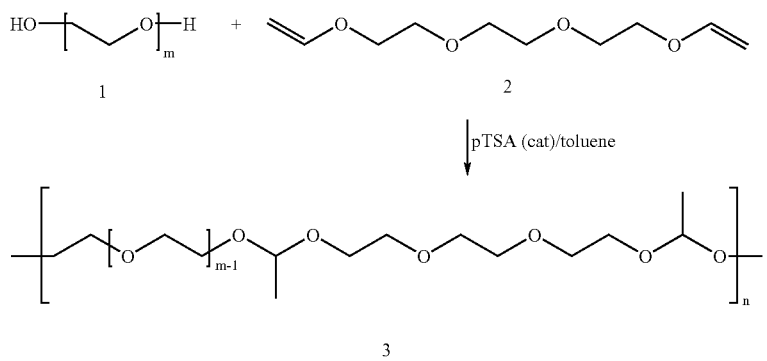

Poly(ethylene glycol) (Mn=3,400 g/mol, 17.0 g, 5.0 mmol, 1.0 eq), para-toluenesulfonic acid monohydrate (0.03 g, 0.15 mmol, 0.03 eq) and toluene (60 ml) were added to a 100 ml round bottom flask which was equipped with a stirring bar and fitted with a thermometer, Dean Stark trap and condenser. An azeotropic distillation of the stirred toluene solution (oil bath, T=150° C.) under nitrogen proceeded for two hours. The solution was then allowed to cool to ~50° C. and tri(ethylene glycol) divinyl ether (1.073 g, 1.083 ml, 5.2 mmol, 1.04 eq) was added by syringe. Within one minute the reaction mixture became visibly more viscous and after 15 minutes the viscosity appeared to be very high. Toluene (30.0 ml) was added to decrease the viscosity and the clear colorless reaction mixture was stirred a further 2 hours at ambient temperature. Aqueous $NaHCO_3$ (8.0%, 2.0 ml) was added to the reaction mixture which was then rapidly stirred for 15 minutes. The aqueous phase was allowed to settle and the toluene phase was carefully decanted into stirred hexane (200 ml) to precipitate the polyacetal. After stirring in the hexane for an additional 10 minutes the polyacetal was collected and placed into a fresh solution of hexane and stirred for a further 10 minutes. The polyacetal was again collected and then dried in vacuum at 50° C. for 4 hours to give a white fluffy solid. The molecular weight was determined to be Mw=42,806 g/mol, Mn=26760 g/mol; polydispersity-1.60 by GPC. The GPC was calibrated with PEG standards; 56,000, 23,500 and 5598 g/mol.

Example 2

Synthesis of Polyacetal 3 by Polymerization in THF

A suspension of $PEG_{3400}$ (1.041 g, 0.306 mmol) and para-toluenesulfonic acid (25 mg) in toluene (50 ml) was heated to reflux; the flask was fitted with a Dean and Stark trap and a balloon of argon was fitted to the condenser. After 150 min most of the toluene was distilled off. To the residue was added the divinyl ether (0.306 mmol, 1.0 eq) in freshly distilled THF (10 ml). The mixture was stirred at room temperature under argon for 16 h. Triethylamine (0.2 ml) was added and the mixture was stirred for 5 minutes. The mixture was poured into hexane (300 ml) with rapid stirring, after 5 min the hexane was decanted off and the residue was washed with further hexane (200 ml) for 30 minutes. The polymer was filtered off.

This same procedure was used for polymerizations conducted in dichloromethane.

Example 3

Synthesis of Bis-vinyl Ethers Useful for Preparing Polyacetals

The vinyl ethers were made from methyl esters using the commercially available amino vinyl ether. This avoided the use of heavy metals to make the vinyl ether moiety.

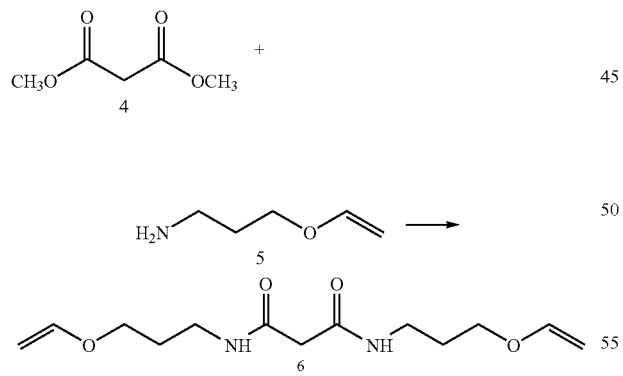

A solution of 3-amino-1-propanol vinyl ether 5 (0.27 mmol, 2.2 eq) and dimethyl malonate 4 (0.12 mmol, 1 eq) in dichloromethane (5.0 ml) was stirred at ambient temperature for 3 days. The reaction mixture was diluted with dichloromethane (50 ml) and washed with water (2×35 ml), conc. NaCl solution (35 ml) and dried over $MgSO_4$. The solvent was evaporated to give a semi-solid residue which was triturated with ether-hexane (1:1) to give the bis vinyl ether 6.

Example 4

Synthesis of Bis-vinyl Ethers Useful for Preparing Polyacetals with Functionality to Conjugate Bioactive Compounds

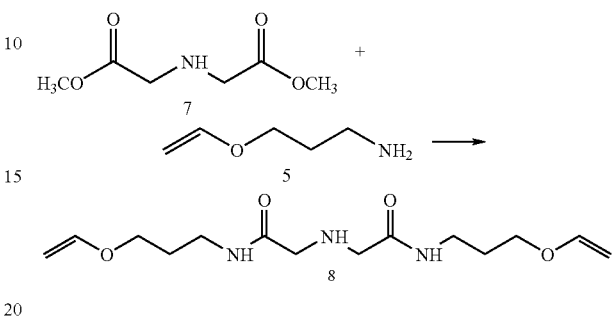

A saturated aqueous $Na_2CO_3$ solution (20 ml) of dimethyl iminodiacetate 7 (10 mmol, 1.0 eq) and 3-amino-1-propanol vinyl ether 5 (40 mmol, 4.0 eq) was stirred for 1 h at 90° C. The solution was cooled and extracted three times with ethyl acetate (80 ml each time). The organic layer was washed with brine, dried over $MgSO_4$, and rotoevaporated to give the bis-vinyl ether 8 as a white crystalline solid.

The bis-vinyl ether 8 was then allowed to react with various acylating agents (e.g. Fmoc protected glycine N-hydroxysuccinimde ester and benzyl chloroformate) to protect (block) the amino functionality in 8 prior to polymerization. The protecting (blocking) group is important because it allows polymerization to proceed without competitive side reactions with the conjugating functionality. After polymerization it must be removed without causing degradation of the polyacetal. This strategy is illustrated in Example 5 for the preparation and polymerization of glutamic acid derived bis-vinyl ether 11 and the subsequent deprotection of the polyacetal.

Example 5

Synthesis of Bis-vinyl Ethers Useful for Preparing Polyacetals with a Protected Primary Amine Functionality (9→11).

Preparation of a Amino Pendant Chain Functionalized Polyacetal using a Pendant Chain Functionalized Bis-vinyl Ether Monomer (11→13)

Synthesis of Fmoc-glutamnyl Chloride 10 (9→10)

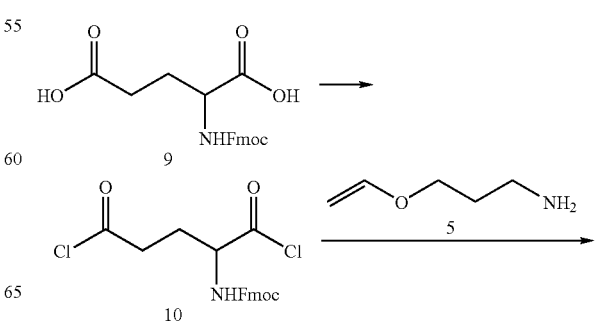

-continued

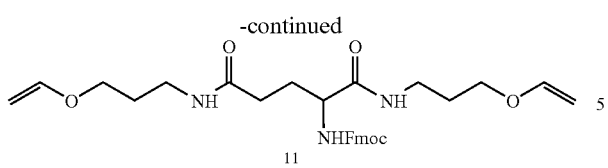

11

To a suspension of Fmoc-glutamic acid 9 (3.13 g, 8.5 mmol) in anhydrous $CH_2Cl_2$ (50 ml) was added oxalyl chloride (5.0 g, 39 mmol). The mixture was cooled to 0° C. and DMF (2 drops) was added. The mixture was stirred at 0° C. for 1 h then at ambient temperature for 1 h under argon atmosphere. Freshly distilled THF (6.0 ml) was added and the mixture was stirred at room temperature for 1 h under argon. Hexane (400 ml) was added and the mixture stirred at ambient temperature for 30 minutes. The hexane was decanted off and the residue recrystallized from $CH_2Cl_2$/hexane to give 10 as white crystals (1.41 g).

Synthesis of Fmoc Glutamic Acid Divinyl Ether 11 (10→11)

To the bis-acid chloride 10 (1.41 g, 3.47 mmol) in anhydrous $CH_2Cl_2$ (25 ml) was added a solution of 3-aminopropyl vinyl ether 5 (701 mg, 6.94 mmol) and $NaHCO_3$ in water (10 ml) dropwise over 5 min with vigorous stirring at 0° C. The mixture was stirred at 0° C. for 10 min then at ambient temperature for 1 hour. The mixture was diluted with $CH_2Cl_2$ (200 ml) then washed with 2% aqueous $NaHCO_3$ (150 ml), brine (150 ml) and then dried with $MgSO_4$. Evaporation gave a pale brown solid which was recrystallized from isopropanol/hexane to yield the divinyl ether 11 as an off white solid (910 mg).

Synthesis of Amino-functionalized Bis-vinyl Ether Monomer 13 (11→3)

A suspension of $PEG_{3400}$ 1 (1.041 g, 0.306 mmol) and p-toluene sulfonic acid (25 mg) in toluene (50 ml) was heated to reflux in a round bottom flask fitted with a Dean and Stark trap to collect the water. After no further increase in water collection was observed, most of the toluene was distilled from the round bottom flask. To the residue was added the divinyl ether 11 (164 mg, 0.306 mmol) in freshly distilled (sodium-benzophenone) THF (10 ml). The mixture was stirred at room temperature under argon for 16 h. Triethylamine (0.2 ml) was added and the mixture was stirred for 5 minutes. The mixture was poured into hexane (300 ml) with rapid stirring to precipitate the polyacetal 12. After 5 min the hexane was decanted off and the polyacetal 12 was stirred with fresh hexane (200 ml) for 30 min. The polyacetal 12 was filtered, collected and dried in vacuum. The weight average molecular weight as determined by GPC (eluent: water, 1 ml/min; PEG standards) was 14300 g/mol. The Fmoc group was removed by dissolving the polymer into an dichloromethane (7% weight percent) followed by the addition of morpholine and the reaction stirred for 15 min at ambient temperature. The amino functionalized polyacetal 13 was precipitated into a stirred solution of hexane (200 ml).

Example 6

Synthesis of a Symmetric, Achiral Bis-vinyl Ether 16 with a Protected Primary Amine Useful for Preparing Polyacetals with Functionality to Conjugate Bioactive Compounds

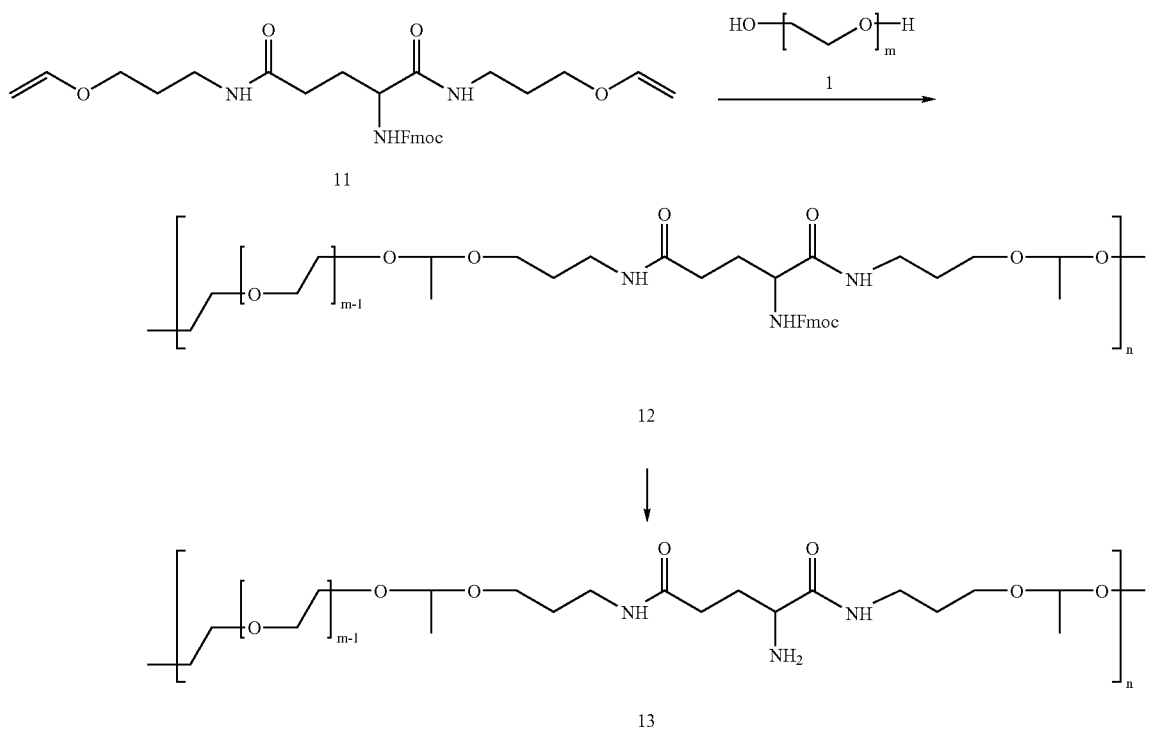

29

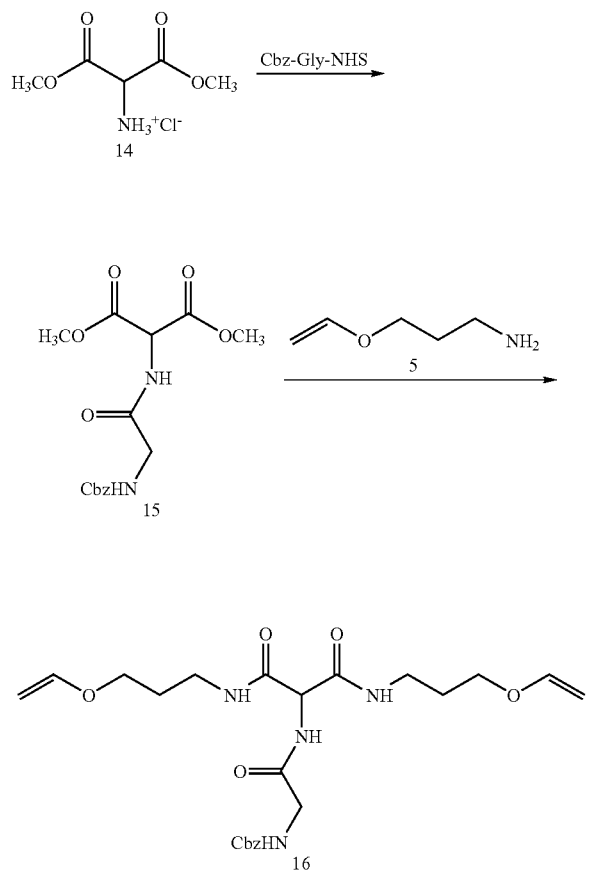

A solution of Cbz-gly-NHS (0.75 g, 2.5 mmol), dimethyl aminomalonate hydrochloride 14 (0.45 g, 2.5 mmol) and triethylamine (0.375 ml) in dichloromethane (5 ml) was stirred in a 25 ml single neck round bottomed flask at ambient temperature for 12 hours. A white precipitate assumed to be triethylamine hydrochloride was evident. The reaction mixture was diluted in dichloromethane (80 ml) and transferred to a separatory funnel, and washed with water and brine. The organic layer was dried over MgSO₄ filtered and the solvent removed by rotoevaporation to give the amino acid dimethylmalonate 15 as white solid (83%). Synthesis of bis-vinyl ether 16 was completed in dichloromethane by the same process as for the preparation of bis-vinyl ether 8 (Example 4).

30

Example 7

Preparation and in vitro Biocompatibility Evaluation of a Pendant Chain Functionalized Polyacetal 22.

This example describes the preparation of a pendant chain functionalized polyacetal. This polyacetal 22 was prepared by a terpolymerization process using a suitably functionalized diol monomer 20 for the incorporation of the pendant chain functionality onto the polyacetal. A radiolabel agent was then conjugated to polyacetal 22 to give the labelled conjugate 23 which was used in an in vivo biodistribution study. An in vitro degradation study is also described for polyacetal 22 in this example.

Synthesis of a Diol 20 that is Functionalized to Provide the Pendant Chain in the Final Polyacetal

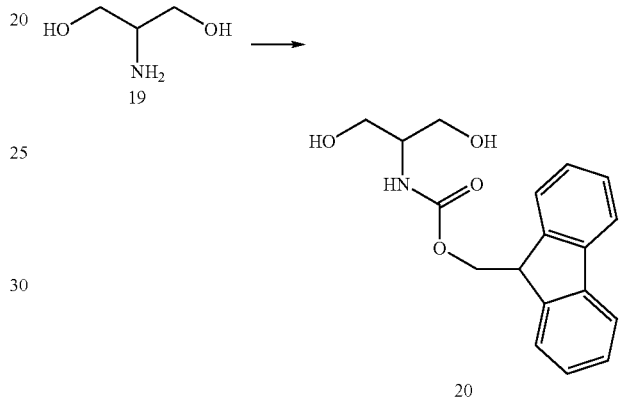

To a rapidly stirred solution of amino diol 19 (1.0 g, 10.0 mmol) and NaOH (1 M, 25 ml) that was cooled to 0–2° C. with a water ice bath was slowly added a dichloromethane (10 ml) solution of Fmoc-chloride (3.4 g, 13.1 mmol, 1.2 eq) over a 1 h period. The solution was stirred a further 1 h at 0° C. then at ambient temperature for 4 h. The reaction mixture was transferred to a rotoevaporator and the dichloromethane was evaporated off. To the aqueous residue was added ethyl acetate (70 ml), the solution transferred to a separatory funnel and the organic layer washed with dilute aqueous HCl solution (5%), dilute NaHCO₃, brine, dried over MgSO₄ and rotoevaporated to give a solid which was recrystallized in chloroform to give the Fmoc protected amino diol 20.

Terpolymerization process to prepare the protected amino functionalized polyacetal 21. This is a polymeric precursor to the desired amine functionalized polyacetal 22

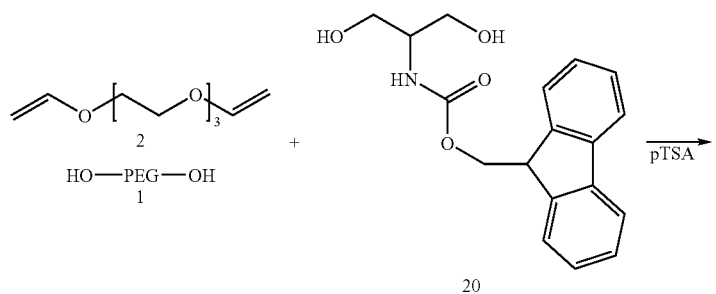

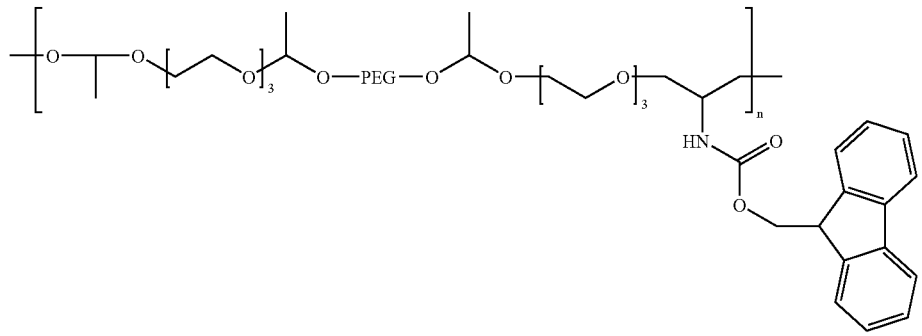

21

PEG$_{3,400}$ 1 (5.005 g, 1.47 mmol, 1.0 eq) and p-toluene sulfonic acid (0.012 g) were added to a 100 ml single neck round bottom flask equipped with a stir bar. This mixture was heated in vacuum (0.5–1.0 torr) at a temperature of 80–90° C. (oil bath) for 3.0 h. After cooling the flask was purged with nitrogen and Fmoc serinol 20 (0.461 g, 1.47 mmol 1.0 eq) and freshly distilled THF (10.0 ml; distilled from sodium-benzophenone) were added to the flask. To this stirred solution was added a solution of tri(ethylene glycol) 2 (0.601 ml, 2.94 mmol, 2.0 eq) in THF (10.0 ml). The reaction mixture was vigorously stirred at ambient temperature for 2 hour, then triethylamine (0.3 ml) was added to deprotonate the p-toluene sulfonic acid. The reaction mixture was slowly added to a stirred solution of hexane (100 ml) to precipitate the polyacetal 21 which was filtered, collected and dried in vacuum at ambient temperature. GPC analysis indicated the molecular weight was about 25,000 g/mol (eluent: phosphate buffer solution, 1 ml/min; 2 Waters Hydrogel Columns; PEG standards). H-NMR analysis confirmed the equivalent incorporation of the Fmoc-amino diol monomer 20 and PEG into the polyacetal 21. The removal of the Fmoc group is given below.

A solution of polyacetal 21 (2.050 g) in 20% piperidine in dichloromethane (10 ml) was stirred at ambient temperature. Thin layer chromatography was used to monitor the reaction (eluent: ethyl acetate). The amino functionalized polyacetal 22 was isolated by first partitioning the piperidine and an unknown amount of by-products into hexane then the dichloromethane was evaporated. The residue was dissolved in THF then this solution added to a stirred solution of hexane (100 ml) to precipitate the desired amino polyacetal 22. GPC analysis indicated the polymer molecular weight to be about 23,000 g/mol (eluent: phosphate buffer solution 1 ml/min; 2 Waters Hydrogel Columns; PEG standards). $^{1}$H-NMR analysis indicated the loss of the aromatic blocking group with no reduction in the acetal functionality.

Conjugation of an Electrophilic Compound to Polyacetal 22

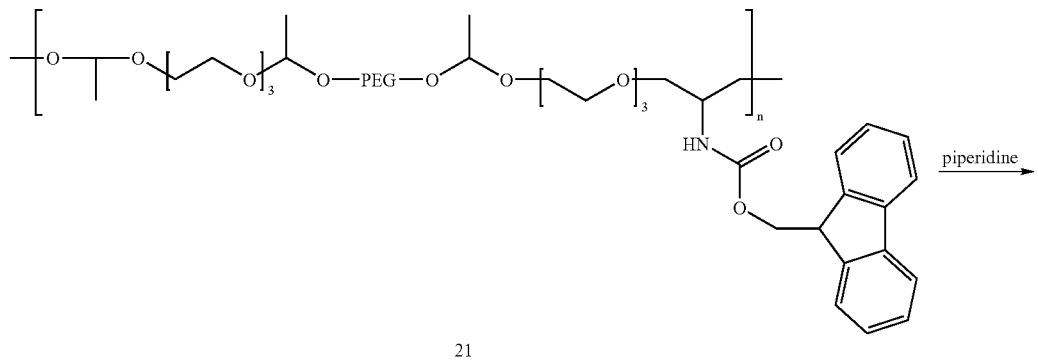

21

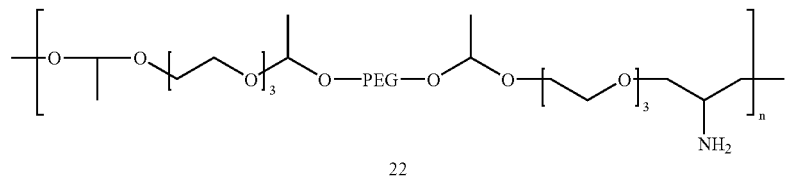

22

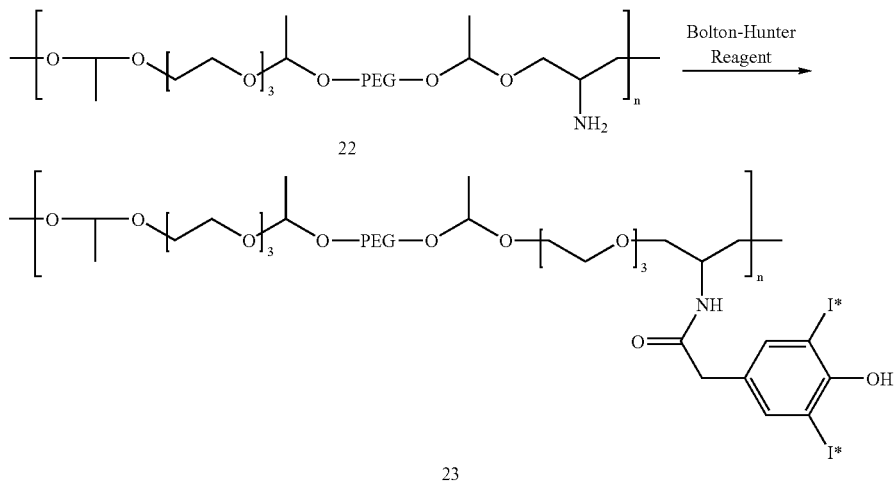

The Bolton-Hunter (N-succinimidyl 3-(4-hydroxy 5-[$^{125}$I]iodophenyl) propionate) method may be used to iodinate peptides which do not contain a tyrosine residue or peptides whose activity is destroyed by tyrosine iodination. See, for example, A. E. Bolton et al., *Biochem. J.*, 133,: 529–38, 1973. The conjugation of Bolton-Hunter radiolabel reagent to the amine functionalized polyacetal 22 gives the conjugated polyacetal 23 which is radiolabeled with $^{125}$I.

The amino polyacetal 22 was radiolabeled using the Bolton Hunter reagent by first dissolving polyacetal 22 (50 mg) at 10 mg/mL in borate buffer (0.1 M) at pH 8.5 by the addition of a small amount of NaOH. To this stirred solution was added a solution of the Bolton Hunter reagent (500 µCi) in benzene with 2% v/v DMF. The reaction mixture was stirred for 15 minutes at ambient temperature and a small aliquot removed (10 µl) as an archive sample and to determine labeling efficiency. The remaining reaction mixture was diluted with phosphate buffer solution (PBS) to 10 ml, transferred to dialysis tubing (molecular mass cut-off 1000 g/mol) and dialyzed against water (5.01) until no radioactivity was found in the dialysate. The water was changed twice daily over a three day period. Following dialysis the quantity of free iodide [$^{125}$I] remaining in the preparation was determined by paper electrophoresis and the 10 ml solution containing the radiolabeled polyacetal 23 was transferred to a vial and stored at −18° C.

The labeling efficiency as determined by paper electrophoresis is shown in FIGS. 5 (crude product) and 6 (purified product 23). The body distribution in the rat of the radiolabeled polyacetal 22 is shown in FIG. 7.

What is claimed is:

1. A polymer-drug conjugate comprising a polymer of Formula (I)

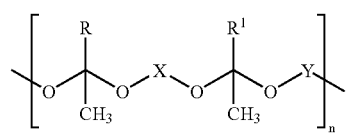

(I)

wherein
R and R1 are independently selected from the group consisting of hydrogen, $C_{1-18}$ alkyl, $C_{2-18}$ alkenyl, $C_{2-18}$ alkynyl, $C_{6-18}$ aryl, $C_{7-18}$ alkaryl and $C_{7-18}$ aralkyl groups;
X is selected from the groups (IV)–(VIII)

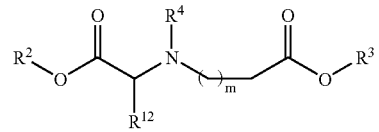

(IV)

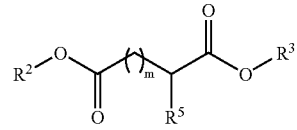

(V)

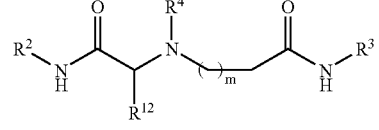

(VI)

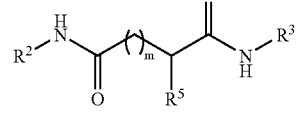

(VII)

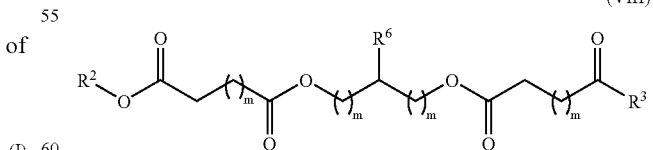

(VIII)

wherein
$R^2$ and $R^3$ are selected from covalent bonds or $C_{1-18}$ alkanediyl groups;
$R^{12}$ are selected from synthetic or natural amino acid side chains;

R⁴ is selected from the group consisting of hydrogen, activating/protecting groups, and the groups (IX), (X), (XI) and (XII),

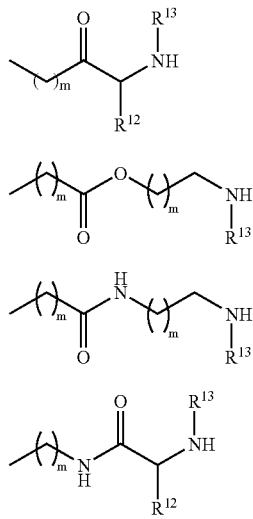

R⁵ and R⁶ are selected from the group consisting of —NH₂, —NHR¹³, —OR¹⁴;

R¹³ and R¹⁴ are selected from activating/protecting groups consisting of N-succinimidyl, pentachlorophenyl, pentafluorophenyl, para-nitrophenyl, dinitrophenyl, N-phthalimido, N-norbonyl, cyanomethyl, pyridyl, trichlorotriazine, 5-chloroquinilino, and protecting groups such as N-(9-fluorenyl-methoxycarbonyl) (Fmcx), carbobenzyloxy (Cbz), 1-(4,4-dimethyl-2,6-dioxocyclohexyldene)-ethyl (Dde) and imidazolyl; and m is an integer of 0-20; wherein X is covalently conjugated to a drug via a peptidic or a hydrolytically-labile bond;

Y is —(C$_n$H$_{2n}$O)$_q$, C$_n$H$_{2n}$-, wherein n is an interger of 2–10 and q is an interger of 1 to 200.

2. The polymer-drug conjugate of claim 1 wherein the drug is an anti-cancer agent selected from a group consisting of doxorubicin, daunomycin, paclitaxel, and taxotere.

3. The polymer-drug conjugate of claim 2 wherein the drug is doxorubicin.

4. A process for the preparation of a polymer-drug conjugate comprising a polymer of Formula (I)

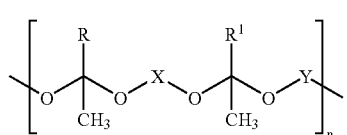

wherein
R and R1 are independently selected from the group consisting of hydrogen, C$_{1-18}$ alkyl, C$_{2-18}$ alkenyl, C$_{2-18}$ alkynyl, C$_{6-18}$ aryl, C$_{7-18}$ alkaryl and C$_{7-18}$ aralkyl groups;

X is selected from the groups (IV)–(VIII)

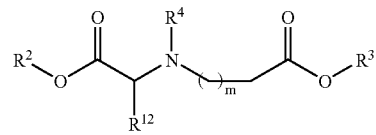

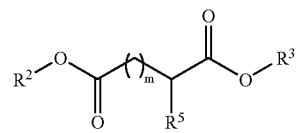

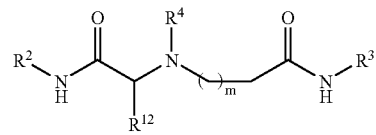

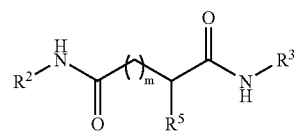

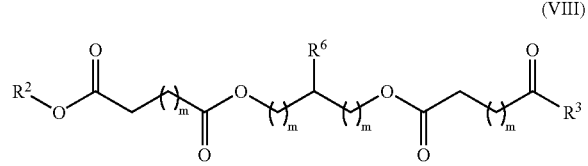

wherein
R² and R³ are selected from covalent bonds or C$_{1-18}$ alkanediyl groups;
R¹² are selected from synthetic or natural amino acid side chains;
R⁴ is selected from the group consisting of hydrogen, activating/protecting groups, and the groups (IX), (X), (XI) and (XII),

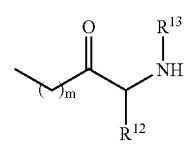

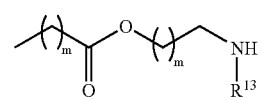

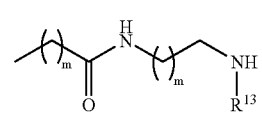

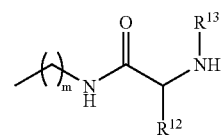

R⁵ and R⁶ are selected from the group consisting of —NH₂, —NHR¹³, —OR¹⁴;

R$^{13}$ and R$^{14}$ are selected from activating/protecting groups consisting of N-succinididy, pentachlorophenyl, pentafluorophenyl, para-nitrophenyl, dinitrophenyl, N-phthalimido, N-norbomyl, cyanomethyl, pyridyl, trichlorotriazine, 5-chloroquinoline, and protecting groups such as N-(9-fluoroenyl-methoxycarbonyl) (Fmox), carbobenzyloxy (Cbz), 1-(4,4-dimethyl-2,6-dixoycyclohexyldene)-ethyl (Dde) and imidazolyl; and m is an integer of 0–20, wherein X is covalently conjugated to a drug via a peptidic or a hydrolytically-labile bond;

Y is —(C$_n$H$_{2n}$O)$_q$, C$_n$H$_{2n}$-, wherein n is an interger of 2–10 and q is an interger of 1 to 200.

5. The process of claim 4 wherein the drug is an anti-cancer agent selected from a group consisting of doxorubin, daunomycin, paclitaxel and taxotere.

6. A pharmaceutical composition comprising a polymer-drug conjugate comprising a polymer of Formula (I)

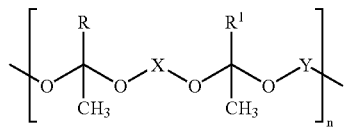

(I)

wherein

R and R$^1$ are independently selected from the group consisting of hydrogen, C$_{1-18}$ alkyl, C$_{2-18}$ alkenyl, C$_{2-18}$ alkynyl, C$_{6-18}$ aryl, C$_{7-18}$ alkaryl and C$_{7-18}$ aralkyl groups;

X is selected from the groups (IV)–(VIII)

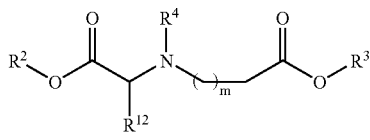

(IV)

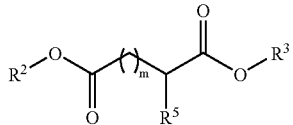

(V)

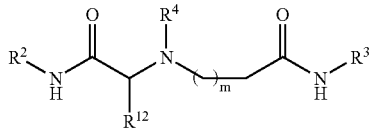

(VI)

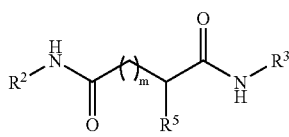

(VII)

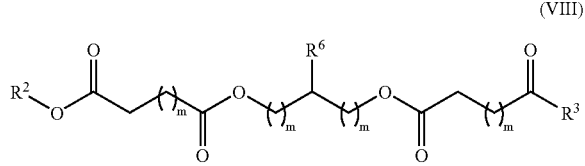

(VIII)

wherein

R$^2$ and R$^3$ are selected from covalent bonds or C$_{1-18}$ alkanediyl groups;

R$^{12}$ are selected from synthetic or natural amino acid side chains;

R$^4$ is selected from the group consisting of hydrogen, activating/protecting groups, and the groups (IX), (X), (XI) and (XII),

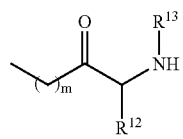

(IX)

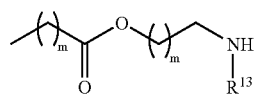

(X)

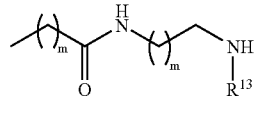

(XI)

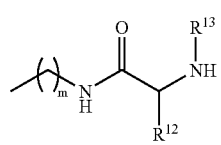

(XII)

R$^5$ and R$^6$ are selected from the group consisting of —NH$_2$, —NHR$^{13}$, —OR$^{14}$;

R$^{13}$ and R$^{14}$ are selected from activating/protecting groups consisting of N-succinididy, pentachlorophenyl, pentafluorophenyl, para-nitrophenyl, dinitrophenyl, N-phthalimido, N-norbomyl, cyanomethyl, pyridyl, trichlorotriazine, 5-chloroquinoline, and protecting groups such as N-(9-fluoroenyl-methoxycarbonyl) (Fmoc), carbobenzyloxy (Cbz), 1-(4,4-dimethyl-2,6-dixoycyclohexyldene)-ethyl (Dde) and imidazolyl; and m is an integer of 0–20, wherein X is covalently conjugated to a drug via a peptidic or a hydrolytically-labile bond;

Y is —(C$_n$H$_{2n}$O)$_q$, C$_n$H$_{2n}$-, wherein n is an interger of 2–10 and q is an interger of 1 to 200.

7. The pharmaceutical composition of claim 6 wherein the drug is an anti-cancer agent selected from a group consisting of doxorubin, daunomycin, paclitaxel and taxotere.

* * * * *